(12) United States Patent
Baudouin et al.

(10) Patent No.: US 10,837,958 B2
(45) Date of Patent: Nov. 17, 2020

(54) METHOD FOR EVALUATING THE HARMFUL EFFECTS OF URINE ON CHILDREN'S SKIN

(71) Applicant: LABORATOIRES EXPANSCIENCE, Courbevoie (FR)

(72) Inventors: Caroline Baudouin, Rambouillet (FR); Philippe Msika, Versailles (FR)

(73) Assignee: LABORATOIRES EXPANSCIENCE, Paris (FR)

( * ) Notice: Subject to any disclaimer, the term of this patent is extended or adjusted under 35 U.S.C. 154(b) by 61 days.

(21) Appl. No.: 15/128,717

(22) PCT Filed: Mar. 31, 2015

(86) PCT No.: PCT/EP2015/057119
§ 371 (c)(1),
(2) Date: Sep. 23, 2016

(87) PCT Pub. No.: WO2015/150426
PCT Pub. Date: Oct. 8, 2015

(65) Prior Publication Data
US 2017/0241989 A1 Aug. 24, 2017
US 2018/0149640 A2 May 31, 2018

(30) Foreign Application Priority Data
Mar. 31, 2014 (FR) .................................... 14 52803

(51) Int. Cl.
| | | |
|---|---|---|
| *C12Q 1/68* | (2018.01) | |
| *G01N 33/50* | (2006.01) | |
| *C12Q 1/6883* | (2018.01) | |
| *G01N 33/68* | (2006.01) | |

(52) U.S. Cl.
CPC ....... *G01N 33/5088* (2013.01); *C12Q 1/6883* (2013.01); *G01N 33/5023* (2013.01); *G01N 33/6881* (2013.01); *C12Q 2600/136* (2013.01); *C12Q 2600/158* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 4,849,077 A | 7/1989 | Rosenthal et al. | |
| 4,882,127 A | 11/1989 | Rosenthal et al. | |
| 6,503,525 B1 * | 1/2003 | Paul ................. | A61F 13/15203 424/402 |
| 6,723,513 B2 | 4/2004 | Lexow | |
| 7,556,922 B2 | 7/2009 | Block et al. | |
| 2002/0119173 A1* | 8/2002 | Lin ........................ | A61K 8/31 424/401 |
| 2006/0275782 A1 | 12/2006 | Gunderson et al. | |
| 2007/0148771 A1 | 6/2007 | Chopart et al. | |
| 2007/0202491 A1* | 8/2007 | Hendrix ............. | G01N 33/5091 435/4 |
| 2008/0020392 A1 | 1/2008 | Block et al. | |
| 2009/0181385 A1 | 7/2009 | McKernan et al. | |
| 2009/0181860 A1 | 7/2009 | McKernan et al. | |
| 2009/0186349 A1 | 7/2009 | Gunderson et al. | |
| 2010/0099576 A1 | 4/2010 | Comer et al. | |
| 2011/0020857 A1 | 1/2011 | Honkonen et al. | |

FOREIGN PATENT DOCUMENTS

| | | |
|---|---|---|
| EP | 0 296 78 A1 | 6/1981 |
| EP | 0 285 471 A1 | 10/1988 |
| EP | 0 789 074 B1 | 8/1997 |
| EP | 1 141 399 B1 | 10/2001 |
| EP | 1 451 302 B1 | 9/2004 |
| EP | 1 878 790 B1 | 1/2008 |
| EP | 1 974 718 B1 | 10/2008 |
| FR | 2938193 B1 | 11/2008 |
| WO | 2001091821 A1 | 12/2001 |
| WO | WO-01/92322 A1 | 12/2001 |
| WO | WO-02/070729 A2 | 9/2002 |
| WO | WO-03/066896 A2 | 8/2003 |
| WO | WO-2006/063864 A1 | 6/2006 |
| WO | WO-2006/063865 A2 | 6/2006 |
| WO | WO-2006/084132 A1 | 8/2006 |
| WO | WO-2007/064305 A1 | 6/2007 |
| WO | WO-2007/111924 A1 | 10/2007 |

(Continued)

OTHER PUBLICATIONS

Auxenfans et al., "Adipose-derived stem cells (ASCs) as a source of endothelial cells in the reconstruction of endothelialized skin equivalents", Journal of Tissue Engineering and Regenerative Medicine, vol. 6, 2012, pp. 512-518.

Auxenfans et al., "Evolution of three dimensional skin equivalent models reconstructed in vitro by tissue engineering", European Journal of Dermatology, vol. 19, No. 2, 2009, pp. 107-113.

Bechetoille et al., "Effects of Solar Ultraviolet Radiation on Engineered Human Skin Equivalent Containing Both Langerhans Cells and Dermal Dendritic Cells", Tissue Engineering, vol. 13, No. 11, 2007, pp. 2667-2679.

Black et al., "Optimization and Characterization of an Engineered Human Skin Equivalent", Tissue Engineering, vol. 11, No. 5/6, 2005, pp. 723-733.

Chiou et al., "Stratum Corneum Maturation: A Review of Neonatal Skin Function", Skin Pharmacology and Physiology, vol. 17, 2004, pp. 57-66.

(Continued)

*Primary Examiner* — Catherine S Hibbert
(74) *Attorney, Agent, or Firm* — Potomac Law Group, PLLC

(57) ABSTRACT

The invention relates to biomarkers of the skin of children and, in particular, that of infants, having altered expression in the presence of urine. Such markers are particularly advantageous as they allow the skin's response to urine to be monitored. The inventors have developed methods for evaluating the efficacy in vitro of formulations in preventing the harmful effects of urine on a child's skin, using a skin model specifically capable of reproducing the characteristics of children's skin.

21 Claims, 3 Drawing Sheets

(56) References Cited

FOREIGN PATENT DOCUMENTS

WO     WO-2014/009566 A1     1/2014

OTHER PUBLICATIONS

Figure 1:
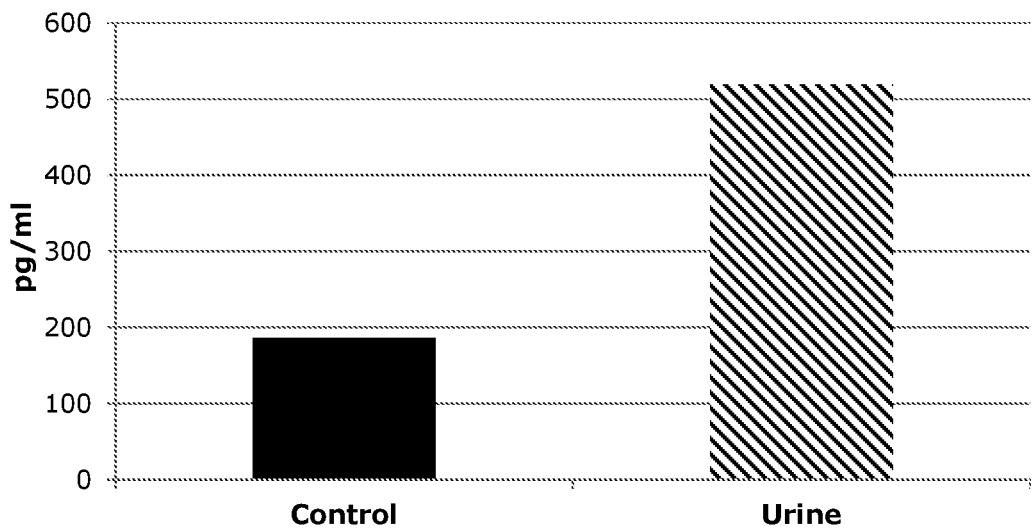

Costin et al., "Vaginal Irritation Models: The Current Status of Available Alternative and In Vitro Tests", ATLA, vol. 39, 2011, pp. 317-337.

Degouy et al., "Baby care product development: Artificial urine in vitro assay is useful for cosmetic product assessment", Toxicology in Vitro, vol. 28, 2014, pp. 3-7.

Dongari-Bagtzoglou et al., "Development of a highly reproducible three-dimensional organotypic model of the oral mucosa", Nat Protoc, vol. 1, No. 4, 2006, 15 pages.

Eisenberg et al., "Human housekeeping genes are compact", Trends in Genetics, vol. 19, No. 7, 2003, pp. 362-365.

Fluhr et al., "Comparaison de la physiologie cutanee du nouveau-ne et du jeune enfant a celle de l'adulte: Etude Clinique randomisee" British Journal of Dermatology, 2014, doi: 10.1111/bjd.12880.

Fluhr et al., "Development and Organization of Human Stratum Corneum After Birth. Electron Microscopy Isotropy Score and Immunocytochemical Corneocyte Labelling as Epidermal Maturation's Markers in Infancy", British Journal of Dermatology, 2014.

Fluhr et al., "Infant epidermal skin physiology: adaptation after birth," British Journal of Dermatology, vol. 166, 2012, pp. 483-490.

Fortunel et al., "Cellular adhesion on collagen: a simple method to select human basal keratinocytes which preserves their high growth capacity", European Journal of Dermatology, 2011, 25 pages.

Fuller et al., "The challenges of sequencing by synthesis", Nature Biotechnology, vol. 27, No. 11, 2009, pp. 1013-1023.

Guenou et al., "Human embryonic stem cells derivatives enable full reconstruction of the pluristratified epidermis", Lancet, vol. 374, 2009, pp. 1745-1753.

Hogan et al., "Skin Barrier Function and Its Importance at the Start of the Atopic March", Journal of Allergy, vol. 2012, 7 pages.

Katoh et al., "Assessment of human epidermal model LabCyte EPI-MODEL for in vitro skin irritation testing according to European Centre for the Validation of Alternative Methods (ECVAM)-validated protocol", The Journal of Toxicological Sciences, vol. 34, No. 3, 2009, pp. 327-334.

Kinikoglu et al., "Reconstruction of a full-thickness collagen-based human oral mucosal equivalent", Biomaterials, vol. 30, No. 32, 2009, pp. 6418-6425.

Kinikoglu et al., "The influence of elastin-like recombinant polymer on the self-renewing potential of a 3D tissue equivalent derived from human lamina propria fibroblasts and oral epithelial cells", Biomaterials, vol. 32, No. 25, 2011, pp. 5756-5764.

Kraehenbuehl et al., "Three-dimensional biomaterials for the study of human pluripotent stem cells", Nature Methods, vol. 8, No. 9, 2011, pp. 731-736.

Lequeux et al., "A Simple Way to Reconstruct a Human 3-D Hypodermis: A Useful Tool for Pharmacological Functionality," Skin Pharmacology and Physiology, vol. 25, No. 1, 2012, pp. 47-55.

Mardis, Elaine "New strategies and emerging technologies for massively parallel sequencing: applications in medical research", Genome Medicine, vol. 1, No. 40, 2009, pp. 40-40.4.

Metzker, Michael "Sequencing technologies—the next generation", Nature Review: Genetics, vol. 11, 2010, pp. 31-46.

Nikolovski et al., "Barrier Function and Water-Holding and Transport Properties of Infant Stratum Corneum Are Different from Adult and Continue to Develop through the First Year of Life", Journal of Investigative Dermatology, vol. 128, 2008, pp. 1728-1736.

Nissan et al., "Functional melanoctyes derived from human pluripotent stem cells engraft into pluristratified epidermis", PNAS, vol. 108, No. 36, 2011, pp. 14861-14866.

Pihlak et al., "Rapid genome sequencing with short universal tiling probes", Nature Biotechnology, vol. 26, No. 6, 2008, pp. 676-684.

Ponec et al., "Lipid and ultrastructural characterization of reconstructed skin models", International Journal of Pharmaceutics, vol. 203, 2000, pp. 211-225.

Ponec et al., "The Formation of Competent Barrier Lipids in Reconstructed Human Epidermis Requires the Presence of Vitamin C", Journal of Investigative Dermatology, vol. 109, No. 3, 1997, pp. 348-355.

Poumay et al., "A simple reconstructed human epidermis: preparation of the culture model and utilization in in vitro studies", Arch Dermatol Res, vol. 296, 2004, pp. 203-211.

Robinson et al., "A Strategy for Skin irritation Testing", American Journal of Contact Dermatitis, vol. 13, No. 1, 2002, pp. 21-29.

Rosdy et al., "Retinoic Acid Inhibits Epidermal Differentiation When Applied Topically on the Stratum Corneum of Epidermis Formed In Vitro by Human Keratinocytes Grown on Defined Medium", In Vitro Toxicology, vol. 10, No. 1, 1997, pp. 39-47.

Runeman, Bo "Skin interaction with absorbent hygiene products", Clinics in Dermatology, vol. 26, 2008, pp. 45-51.

Schmalz et al., "Release of prostaglandin E2, IL-6 and IL-8 from human oral epithelial culture models after exposure to compounds of dental materials", European Journal of Oral Sciences, vol. 108, 2008, pp. 442-448.

Shendure et al., "Next-generation DNA sequencing", Nature Biotechnology, vol. 26, No. 10, 2008, pp. 1135-1145.

Slivka et al., "Characterization, Barrier Function, and Drug Metabolism of an In Vitro Skin Model", The Journal of Investigative Dermatology, Nature Publishing Group, vol. 100, No. 1, 1993, pp. 40-46.

Stamatas et al., "Infant skin physiology and development during the first years of life: a review of recent findings based on in vivo studies", International Journal of Cosmetic Science, vol. 33, 2011, pp. 17-24.

Telofski et al., "The Infant Skin Barrier: Can We Preserve, Protect, and Enhance the Barrier?", Dermatology Research and Practice, 2012, 18 pages.

Vahlquist "Markers of Skin Inflammation and Wound healing", Acts Dem Venereol, vol. 80, 2000, p. 161.

Vrana et al., "Development of a Reconstructed Cornea from Collage-Chrondroitin Sulfate Foams and Human Cell Cultures", Investigative Ophthalmology & Visual Science, vol. 49, No. 12, 2008, pp. 5325-5331.

Farage et al., "Dermatologic Effects and Management of Urine and Feces on Infant and Adult Skin," British Journal of Medicine and Medicinal Research, vol. 4, No. 19, pp. 3671-3688, Apr. 2014.

Andersen et al., "Faecal enzymes: in vivo human skin irritation," Contact Dermatitis, vol. 30, pp. 152-158, 1994.

Berg et al., "Etiologic Factors in Diaper Dermatitis: The Role of Urine," Pediatric Dermatology, vol. 3, No. 2, pp. 102-106, Feb. 1986.

Buckingham et al., "Etiologic Factors in Diaper Dermatitis: The Role of Feces," Pediatric Dermatology, vol. 3, No. 2, pp. 107-112, Feb. 1986.

* cited by examiner

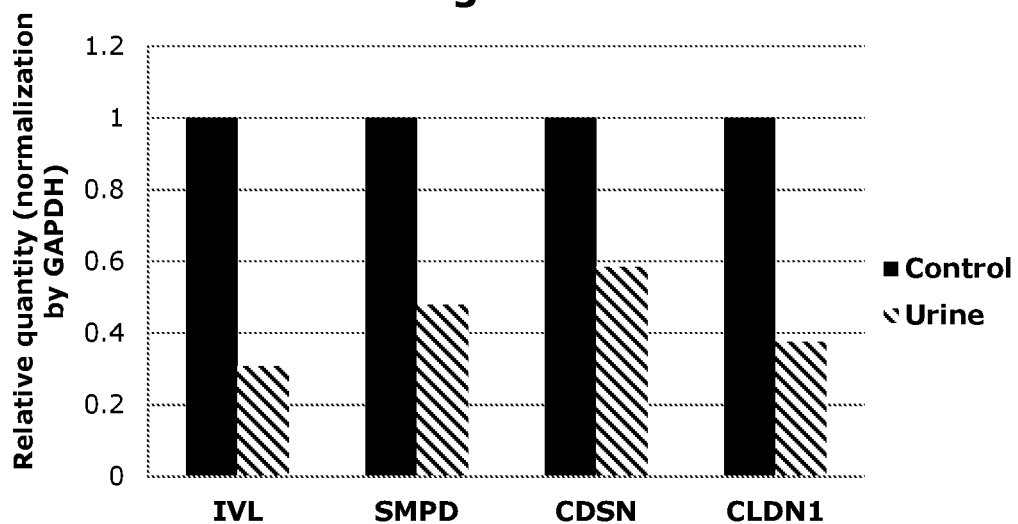
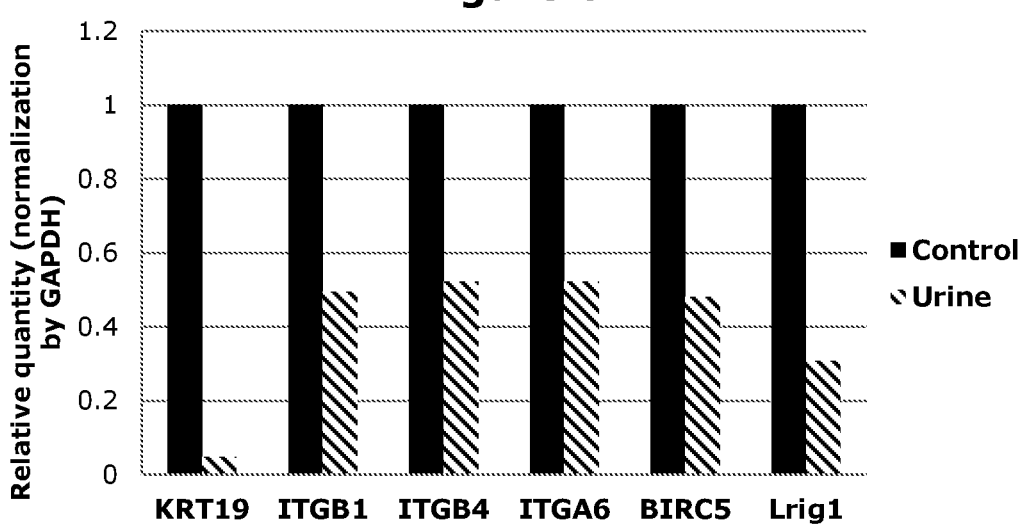

METHOD FOR EVALUATING THE HARMFUL EFFECTS OF URINE ON CHILDREN'S SKIN

The skin is a set of cells and macromolecules grouped together in the form of a resistant and flexible tissue, covering the entire body. It consists of two joined layers, the epidermis and the dermis, with which subcutaneous tissues may be associated.

The epidermis, the principal role of which is that of protecting the body, forms the uppermost layer of the skin and ensures the impermeability and resistance thereof. Four separate cellular layers may be identified in the skin, a basal layer (stratum basalis), a spinous layer (stratum spinosum), a granular layer (stratum granulosum) and a corneal layer (stratum corneum). While various cell types coexist in the epidermis, keratinocytes represent the large majority (90%). The characteristic activity thereof is the synthesis of keratins, fibrous water-insoluble proteins which represent 95% of the total proteins of the epidermis.

The principal function of the skin is to establish a protective barrier against environmental attacks while allowing some exchanges between the internal environment and the external environment. The barrier function is provided first and foremost by the corneal layer, which makes the skin impermeable and hydrophobic, thus protecting the dermis from a massive influx of water. It is also the corneal layer which resists chemical attacks. It is composed of cells, called corneocytes, which are dead and anucleate but filled with keratins and other products such as lipids, fatty acids and ceramides. Corneocytes are joined together by specific tight junctions, corneodesmosomes, forming a compact layer the cohesion of which is further strengthened by a lipid cement. Beneath the granular layer, tight junctions in the granular layer also participate in the skin barrier function (see, for example, Hogan et al., *J Allergy*, 2012: 901940, 2012).

Each day the skin must deal with various attacks. It is exposed, for example, to chemical agents such as soap as well as to physical stresses such as friction against clothing and exposure to the sun. The epidermis and epidermal appendices must thus be constantly renewed to keep the skin in good condition. It is the stem cells which make these maintenance and repair processes possible. More particularly, the regenerative capacity of the epidermis is conferred by adult stem cells which enable the regular replacement of differentiated cells eliminated during keratinization. Epidermal stem cells thus give rise to keratinocytes, which will ultimately differentiate into corneocytes. This process is particularly crucial for barrier function maturation and maintenance.

Adaptation to extrauterine life is a process that begins at birth and continues throughout the first year of life. The first months of postnatal life constitute a period of structural and functional reorganization of the skin which allows physiological adaptation to the extrauterine environment. For example, the immaturity of the skin of newborns is underlined by the different structure and molecular composition of the stratum corneum compared to that of adults. These are incomplete and thus continue to develop during the first 12 months at least after birth (Chiou et al., *Skin Pharmacol Physiol*, 17: 57-66, 2004; Nikolovski et al., *J Invest Dermatol*, 128: 1728-1736, 2008; Stamatas et al., *Pediatr Dermatol*, 27: 125-131, 2010; Telofski et al., *Dermatol Res Pract*, 2012: 198789, 2012). Furthermore, the results of two recent clinical studies (Fluhr et al., *Br J Dermatol*, 166(3): 483-90, 2012 and Fluhr et al., *Br J Dermatol*, 2014, doi: 10.1111/bjd.12880) suggests that the skin of infants has a certain immaturity in its capacity to capture water and to regulate the related mechanisms. In addition, this work showed that the epidermal barrier is organized structurally from birth to 2 years of age and is thus not completely competent during this period. This helps explain the fragility of infants' and young children's skin and the susceptibility thereof to chemical, physical and microbial attacks.

Moreover, incomplete skin maturation can have significant clinical consequences. It is thus important to enable the skin to be built and to develop correctly and harmoniously, without which its functional and structural organization could be compromised. In this respect, it is crucial to preserve the epidermis's barrier function and capacity of renewal.

Diaper rash, or diaper dermatitis, is a dermatological lesion common in babies wearing diapers (one child in three), resulting in skin irritation, that is sometimes painful, appearing where the diaper contacts the skin. It generally results from the conjunction of several factors, the most important being extended contact between the baby's skin and urine. Urine produces ammonia by fermentation and thus will contribute toward modifying skin pH which will then play an important and harmful role in the physiopathology of the diaper rash. Moreover, the effects of urine are added to those of perspiration trapped in skin folds and beneath the diaper which soak the skin, creating a damp and occlusive environment and considerably increasing pH and barrier inflammation and degradation and thus amplifying the risks of friction-generated lesions and thus irritation. In this context, urine thus increases the risk of loss of skin barrier integrity, which may lead to a more serious form of diaper rash, with open wounds which may become infected and which must be treated by a doctor.

The pharmaceutical or cosmetic products available on the market generally contain zinc oxide, vitamins (A, D and D3), or combinations thereof. These active agents are incorporated in a cream or an aqueous paste or an ointment by mixing them with semi-solid bases such as, for example, mineral oils, paraffin, lanolin, etc. They may be used to prevent or reduce the harmful effects of urine, such as diaper rash. However, while some of these products provide relief during episodes of mild redness/irritation, they show only a very relative efficacy against more significant diaper rashes. And purely medicated products often have a pharmacology and a concentration of ingredients which make them difficult to use in the long term as they are potentially irritating or allergenic. Moreover, the purpose of these products is only to alleviate diaper dermatitis, not to preserve the barrier function of the skin or the capacity of renewal of the epidermis. There thus still remains a need, by integrating knowledge of children's skin and the role of aggravating factors (like urine and pH) to identify and characterize active agents and improved formulations for dealing with diaper rash best.

FIGURE LEGENDS

FIG. 1: Production of PGE2, lipid inflammation mediator

Figure 2:
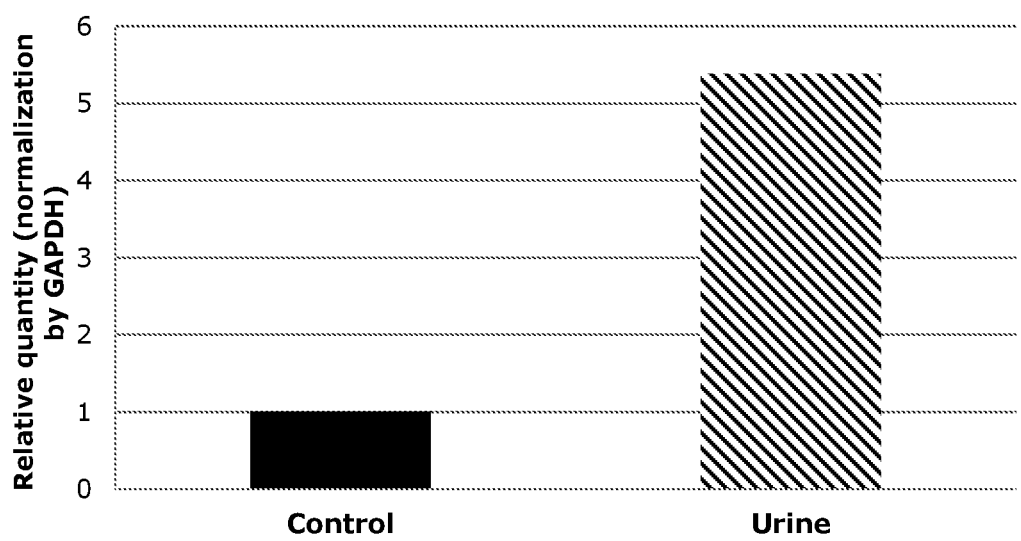

FIG. 2: Expression of the PTGS2 gene, lipid inflammation mediator

Figure 3:
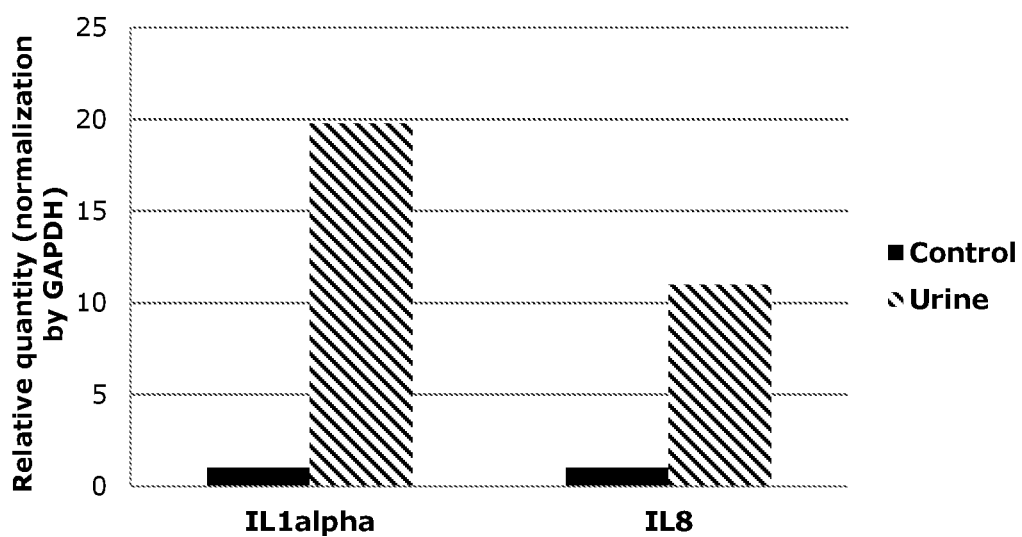

FIG. 3: Expression of the IL1alpha and IL8 genes, protein inflammation mediators FIG. 4: Expression of the TRPV1 and SPR genes, neurogenic inflammation mediators FIG. 5: Expression of the IVL, SMPD, CSN and CLDN1 genes, barrier function markers FIG. 6: Expression of the KRT19, ITGB1, ITGB4, ITGA6, BIRC5, Lrig1 genes, stem cell markers

DESCRIPTION

The present Inventors showed that children's skin, and in particular infants' skin, is particularly sensitive to the harmful action of urine. In particular, they were able to identify biological markers the expression of which is altered in the presence of urine. Such markers are particularly advantageous because they make it possible to follow the skin's response to urine.

The Inventors developed methods for evaluating the in vitro efficacy of active ingredients and formulations in preventing the harmful effects of urine on children's skin, using a skin model specifically able to reproduce the characteristics of children's skin, and in particular that of very young children such as infants. The studies of the prior art rested on the use of adult's skin to analyze the skin's response to urine (Degouy et al., *Toxicol In Vitro*, 28(1): 3-7. 2014). However, the skin's properties evolve during the first years of life (see, for example, Fluhr et al., *Exp Dermatol.*, 19(6): 483-492, 2010; Fluhr et al., *Br J Dermatol*, 166(3): 483-90, 2012 and Fluhr et al., *Br J Dermatol.*, 2014, doi: 10.1111/bjd.12880) and it is unlikely that it is possible to determine precisely the effects of urine on children's skin from samples of adult's skin.

On the other hand, the Inventors developed reconstructed skin models derived from samples from children and were able to test the effect of urine on these models. They were thus able to observe that the expression of certain biological markers was altered when these models of reconstructed children's skin were contacted with urine. Certain markers, such as markers of inflammation, were thus more strongly expressed, whereas the expression of others, such as stem cell markers or those of the barrier function, was decreased. On the other hand, the variations of expression of these markers were reduced, or became less marked, when the models were treated with active agents or formulations known to alleviate diaper rash. This result underlines the physiological relevance of these markers. The importance of the use of models of reconstructed skin from children and not from adults in order to isolate such markers therefrom is further reinforced.

The term "child", according to the invention, refers to an individual under 16 years of age. Thus, the category of children according to the invention includes newborns, between 0 and 1 month of age, infants, between 1 month and 2 years of age, and children per se, at least 2 years of age. A "newborn" as used herein may equally well be born at full term or prematurely.

To remove any ambiguity, the term "child" used in the present application without any further clarification should be understood in the most general meaning thereof, i.e. as referring to a person under 16 years of age. An "adult" according to the present invention is a person who is not a child, in order words a person over 16 years of age.

Preferably, the method according to the invention may be used regardless of the ethnic or geographic origin of the skin, or the phototype thereof. It may thus be of Caucasian, African, Asian, South American, Melanesian or other origin; it may further have the phototype I, II, III, IV, V or VI, without affecting the invention. Indeed, the invention aims at identifying biological markers characterizing any skin type and depending only on the donor's age.

The methods of the invention thus rest on the use of a suitable skin model, reproducing children's skin, as well as the use of biological markers, the expression of which is affected by urine in a particular manner in children's skin. The invention thus makes it possible to determine precisely which active agents have an advantageous effect on the prevention or treatment of the harmful effects caused by contacting the skin with urine. The methods of the invention are also suitable for evaluating the activity of formulations. The Inventors were thus able to show that certain formulations were more effective than others in preventing and/or limiting the effects of urine, thus showing the utility of the approach undertaken.

According to a first aspect, the invention has as an object a method for evaluating the in vitro efficacy of an active agent or a formulation in preventing the harmful effects of urine on children's skin, characterized in that said method comprises the following steps:

a) contacting said active agent or said formulation with a reconstructed skin model, said model being obtained from a skin sample from a child;
  b) exposing the reconstructed skin model of step a) to urine;
  c) measuring the expression level of at least one biological marker in the skin model of step b); and
  d) evaluating the efficacy of said active agent or said formulation as a function of the level of step c).

In a first preferred embodiment, the reconstructed skin model is exposed to urine in step b) in the presence of the active agent or the formulation. According to another preferred embodiment, the active agent or the formulation is removed prior to exposing said reconstructed skin model to urine during said step b).

Furthermore, the invention also has as an object a method for evaluating the in vitro efficacy of an active agent or a formulation in reducing the harmful effects of urine on children's skin, characterized in that said method comprises the following steps:

a) exposing a reconstructed skin model to urine, said model being obtained from a skin sample from a child;
  b) contacting said active agent or said formulation with the reconstructed skin model of step a);
  c) measuring the expression level of at least one biological marker in the skin model of step b); and
  d) evaluating the efficacy of said active agent or said formulation as a function of the level of step c).

Persons skilled in the art will easily understand that steps a) and b) may be carried out simultaneously or successively, according to need. In other words, the reconstructed skin model may be contacted with both urine and the active agent or formulation tested. Alternatively, the skin model may first be exposed to urine, then contacted with the active agent or the formulation.

The expression "the efficacy of a formulation or an active agent in preventing or reducing the harmful effects of urine on children's skin", in the meaning of the present application, refers to the ability of the formulation or the active agent to cancel or decrease said harmful effects on children's skin. Prevention refers in this case to a treatment administered before the harmful effects of urine develop, whereas reduction refers to a treatment administered once the effects of urine appear.

According to a more preferred embodiment, the sample donor is more particularly a donor between 0 and 1 month of age, between 1 month and 2 years of age or between 2 years and 16 years of age. In other words, according to this embodiment, the sample donor is selected from the group consisting of newborns, between 0 and 1 month of age, infants, between 1 month and 2 years of age, and children, between 2 years and 16 years of age. More preferentially, the sample donor is a newborn or an infant.

In a first embodiment, the expression level of said biological marker of step a) is compared to a reference expression level.

It is important to verify that the active agents and the formulations of the invention are well tolerated. For example, certain products currently marketed may cause irritation if used regularly. Such an effect can only worsen a developing or existing diaper rash.

According to another aspect, the invention thus has as an object a method for evaluating the tolerance of an active agent or a formulation when children's skin is exposed to urine, said method comprising the following steps:
 a) contacting said active agent or said formulation with a reconstructed skin model, said model being obtained from a skin sample from a child;
 b) exposing the reconstructed skin model of step a) to urine in the presence of the active agent or the formulation;
 c) measuring the expression level of at least one biological marker in the skin model of step b); and
 d) determining whether said active agent or said formulation is well tolerated by children's skin as a function of the level of step c).

The method of the invention may further comprise a comparison of the cell viability in the reconstructed skin model treated with the active agent, the composition or the formulation and in the control reconstructed skin model, i.e. treated with urine alone. In this case, the active agent or the cosmetic formulation is well tolerated by children's skin if the cell viability of the reconstructed skin model is not affected by the presence of the agent or the formulation.

According to another preferred embodiment, the method of the invention thus comprises an additional step of determining the cell viability in the reconstructed skin model exposed to urine and treated with the active agent or the cosmetic formulation, determining the cell viability of the control reconstructed skin model and comparing the two.

Many tests for determining cell viability are available to persons skilled in the art and are commonly used in cosmetics science. In particular, mention may be made of the MTT test, described for example in Mosman et al. (*J Immunol Methods*, 65(1-2): 55-63, 1983).

In another aspect, the invention makes it possible to isolate formulations or active agents having an effect in preventing the harmful effects of urine on children's skin. As the experimental examples show, the invention makes it possible in particular to distinguish active agents or formulations according to their activity for preventing the harmful effect of urine on children's skin. The invention thus is particularly suited to identifying appropriate formulations or active agents for this very specific skin.

The invention thus also has as an object a method for identifying an active agent or a formulation for preventing the harmful effects of urine on children's skin, characterized in that said method comprises the following steps:
 a) contacting a candidate active agent or formulation with a reconstructed skin model, said model being obtained from a skin sample from a child;
 b) exposing the skin model of step a) to urine;
 c) measuring the expression level of at least one biological marker in the skin model of step b); and
 d) determining whether said candidate active agent or formulation is a formulation or an active agent for preventing the harmful effects of urine on children's skin as a function of the level of step c).

In a first preferred embodiment, the reconstructed skin model is exposed to urine in step b) in the presence of the active agent or the formulation. According to another preferred embodiment, the active agent or the formulation is removed prior to exposing said reconstructed skin model to urine during said step b).

Likewise, the method of the invention makes it possible to isolate active agents or formulations for reducing the harmful effects of urine on children's skin. According to this embodiment, this method comprises the following steps:
 a) exposing a reconstructed skin model to urine, said model being obtained from a skin sample from a child;
 b) contacting a candidate active agent or formulation with the skin model of step a);
 c) measuring the expression level of at least one biological marker in the skin model of step b); and
 d) determining whether said candidate active agent or formulation is a formulation or an active agent for reducing the harmful effects of urine on children's skin as a function of the level of step c).

Persons skilled in the art will easily understand that steps a) and b) may be carried out simultaneously or successively, according to need. In other words, the reconstructed skin model may be contacted with both urine and the active agent or formulation tested. Alternatively, the skin model may be exposed to urine first, then contacted with the active agent or the formulation.

The candidate formulation is a formulation for preventing or reducing the harmful effects of urine on children's skin if said candidate formulation modulates the expression of at least one biological marker of the invention. This modulation may correspond, as the case may be, and in particular according to the nature of the biological marker, to an increase or a reduction in the expression of said marker. For example, it may be advantageous to isolate formulations minimizing the harmful effects of urine on markers preferentially expressed in stem cells, said formulations making it possible to preserve the capacity of renewal of children's fragile skin. Likewise, it would be advantageous to identify formulations minimizing the harmful effects of urine on barrier markers in children, in order to maintain the integrity of the skin barrier. Finally, it could be desirable to isolate formulations that would not induce markers of inflammation.

In the same way, the candidate active agent is an active agent for preventing or reducing the harmful effects of urine on children's skin if said candidate active agent modulates the expression of at least one biological marker of the invention. This modulation may correspond, as the case may be, and in particular according to the nature of the biological marker, to an increase or a reduction in the expression of said marker.

The term "urine" refers to a liquid consisting of about 95% water and about 5% organic matter and mineral salts, mainly acid chlorides, sulfates and phosphates of soda, potassium and magnesium. The organic matter of urine comprises in particular dyes, urea, uric acid and creatinine. Urine is typically produced by the body of vertebrates, preferentially humans, from which it evacuates waste. There exist also artificial or synthetic urines, the composition of which is simplified compared to that of natural urines, but which also come under the definition of the term "urine" as used herein. Methods for manufacturing synthetic urine are well-known to persons skilled in the art. Persons skilled in the art can refer, for example, to patent EP 1 045 707 B1 or to the articles by Shmaefsky, (*Am. Biol. Teacher*, 52: 170-173; 1990; *Am. Biol. Teacher*, 57: 428-430, 1995) and Degouy et al. (*Toxicol In Vitro*, 28(1): 3-7, 2014). Preferably, the synthetic or artificial urine as defined in the present application comprises urea, creatinine, ammonium acetate and citric acid. Thus, the synthetic or artificial urine according to the invention advantageously comprises urea at a concentration between 9 and 24.5 g/l, sodium chloride between 3 and 14 g/l, creatinine between 0.6 to 2.3 g/l, ammonium salts such as, for example, ammonium acetate, between 0.003 and 4.2 g/l and citric acid between 0.09 and 0.95 g/l.

Preferentially, the pH of the synthetic urine according to the invention is between 6 and 10 and more preferentially between 7 and 9; more preferentially, the pH of the synthetic urine according to the invention is equal to 8.

The expression "harmful effects of urine", in the meaning of the present application, refers to pathological reactions ensuing from exposure of the skin to urine. These pathological reactions comprise in particular erythema, i.e. redness, accompanied by a sensation of discomfort and pain, alteration of the barrier and the skin, formation of lesions and desquamation.

In the meaning of the invention, the expression "the efficacy of a formulation in preventing or reducing the harmful effects of urine on children's skin" refers to the ability of the formulation to decrease at least one of the above-mentioned harmful effects.

First, the formulation or active agent of interest is contacted with a reconstructed skin culture obtained from a sample from a child. This contacting of the active agent of interest with the skin model may be made directly. Alternatively, it could be advantageous to formulate the active agent of interest, for example so as to obtain a liquid composition, in order to facilitate its contact with the skin model. Thus, according to an embodiment of the invention, the method further comprises a step of formulating the active agent, in particular in the form of a liquid solution, in particular an aqueous solution, prior to the step of contacting said active agent with a skin model.

The Inventors previously showed that the expression profiles of specific categories of genes (for example, barrier, inflammation, defense and stem cell genes) evolve as a function of age (application PCT/EP2013/064926). Persons skilled in the art can thus easily characterize skin at the molecular level from birth to adulthood. More particularly, persons skilled in the art will note that children's skin cells have a specific expression profile of genes involved in specific physiological processes, in particular cell metabolism, the stress response, inflammation, immunity, apoptosis, growth/proliferation and the cell cycle, cell signaling, migration and differentiation, the epidermal barrier, adhesion and pluripotent stem cells of the skin.

In the meaning of the invention, the reconstructed skin model obtained from a skin sample from a child may be any tissue model comprising skin cells, in particular keratinocytes, and wherein said skin cells were obtained from a sample from a child.

The term "skin sample", in the meaning of the invention, refers to any sample containing skin cells. The skin samples according to the invention thus include fresh skin explants obtained directly from the patient, suspended skin cell cultures, monolayer skin cell cultures, bilayer skin cell cultures and tissue models, including reconstructed skin cultures and reconstructed mucosal cultures. As it is often difficult to work on fresh explants, it is particularly advantageous, within the scope of the present invention, to use skin cell cultures. Advantageously, the skin cells according to the invention comprise normal, healthy or diseased cells, or cells derived from lines. For example, the skin cells placed in culture may be cells obtained from skin, tissue explant. The term "explant" or "skin explant" as used herein refers to a sample of skin cells or tissue, which may be obtained for surgical purposes or to perform analyses.

In particular, an explant may be obtained during surgical excision. The term "excision" as used herein refers to a surgical procedure consisting of cutting (excising) a portion of varying width and depth of skin in order to treat a defect or growth thereof. Excision is performed either to remove a cancerous or suspected cancerous tumor, or to treat a benign skin defect which is unwanted, for functional or cosmetic reasons. An excision according to the invention includes for example skin samples obtained after plastic surgery (mammoplasty, abdominoplasty, face-lift, foreskin removal, otoplasty, i.e. ear pinback, syndactyly or supernumerary fingers, etc.).

An explant also may be obtained by biopsy. The term "biopsy" as used herein refers to a sample of skin cells or tissue taken for the purposes of analysis. Several types of biopsy procedures are known and performed in the field. The most common types include (1) incisional biopsy, wherein only a tissue sample is taken; (2) excisional biopsy (or surgical biopsy) consisting of total ablation of a tumor growth, thus carrying out a therapeutic and diagnostic procedure, and (3) needle biopsy, wherein a tissue sample is taken with a needle, which may be wide or fine. Further types of biopsies exist, such as for example smears or curettage, and are also included in the present invention.

Alternatively, said skin cells may be obtained by stem cell differentiation (Guenou et al., *Lancet*, 374(9703): 1745-1753, 2009; Nissan et al., *Proc. Natl. Acad. Sci.*, 108(36): 14861-14866, 2011; Kraehenbuehl et al., *Nature Methods*, 8: 731-736, 2011).

The skin cells according to the invention, whether obtained from a biopsy or obtained by stem cell differentiation, include at least one type of cells habitually present in the hypodermis, dermis and/or epidermis. These cells thus include, among others, keratinocytes, melanocytes, fibroblasts, adipocytes, endothelial cells, mast cells, Langerhans cells and/or Merkel cells. Preferentially, the skin cells according to the invention include at least keratinocytes and/or fibroblasts. More preferentially, the skin cells according to the invention include keratinocytes and/or fibroblasts.

Numerous skin cell culture methods are known to persons skilled in the art. Any of these methods may be used to culture the skin cells according to the invention. Advantageously, the skin cells are cultured and/or stored under conditions maintaining, at least partially, a cell metabolism and/or cell functions. The skin cell culture according to the invention thus includes equally well suspended skin cell cultures, monolayer skin cell cultures, bilayer skin cell cultures and tissue models, including reconstructed skin cultures and reconstructed mucosal cultures.

For example, suspended skin cell cultures are routinely employed in a very large number of laboratories, for several decades. Similarly, monolayer or bilayer skin cell cultures have been known and used for a very long time.

Furthermore, numerous tissue models, including in particular reconstructed skin models and reconstructed mucosal models (Rosdy et al., *In Vitro Toxicol.*, 10(1): 39-47, 1997; Ponec et al., *J Invest Dermatol.*, 109(3): 348-355, 1997; Ponec et al., *Int J Pharm.*, 203(1-2): 211-225, 2000; Schmalz et al., *Eur J Oral Sci.*, 108(5): 442-448, 2000; Black et al., *Tissue Eng*, 11(5-6): 723-733, 2005; Dongari-Batgtzoglou et Kashleva, *Nat Protoc*, 1(4): 2012-2018, 2006; Bechtoille et al., *Tissue Eng*, 13(11): 2667-2679, 2007; Vrana et al., *Invest Ophthalmo(Vis Sci,* 49(12): 5325-5331, 2008; Kinicoglu et al., *Biomaterials,* 30(32): 6418-6425, 2009; Auxenfans et al., *Eur J Dermatol,* 19(2): 107-113, 2009; Kinicoglu et al., *Biomaterials,* 32(25): 5756-5764, 2011; Costin et al., *Altern Lab Anim,* 39(4): 317-337, 2011; Auxenfans et al., *J Tissue Eng Regen Med,* 6(7): 512-518, 2012; Lequeux et al., *Skin Pharmacol Physiol,* 25(1): 47-55, 2012; EP 29 678; EP 285 471; EP 789 074; EP 1 451 302 B1; EP 1 878 790 B1; EP 1 974 718; US 2007/0148,771; US 2010/0,099,576; WO 02/070729; WO 2006/063864; WO 2006/063865; WO 2007/064305) are available to persons skilled in the art and are included in the scope of the invention.

Advantageously, the tissue model comprises reconstructed skin models and reconstructed mucosal models. Preferably, the reconstructed skin model is selected from the group comprising dermis models, principally containing stromal cells, and more particularly fibroblasts, epidermis models essentially consisting of keratinocytes, hypodermis models, skin models including a dermis and an epidermis, and skin models comprising a dermis, an epidermis and a hypodermis. The models comprising at least a dermis form connective type tissues, whereas the models comprising at least an epidermis form stratified epithelia comprising characteristic layers of the tissue in question. For example, in the epidermis models, it is possible to identify a basal layer (stratum basalis), a spinous layer (stratum spinosum), a granular layer (stratum granulosum) and a corneal layer (stratum corneum). Furthermore, preferably, the reconstructed mucosal model according to the invention is a mucosal model of the mouth, gum, vagina or cornea.

Advantageously, said model is a; connective type tissue model of dermal matrix comprising a matrix substrate preferably selected from:
  an inert substrate selected from the group consisting of a semi-permeable synthetic membrane, in particular a semi-permeable nitrocellulose membrane, a semi-permeable nylon membrane, a Teflon membrane or sponge, a polycarbonate or polyethylene, polypropylene, semi-permeable polyethylene terephthalate (PET) membrane, an inorganic semi-permeable Anopore, cellulose acetate or ester (HATF) membrane, a semi-permeable Biopore-CM membrane, a semi-permeable polyester membrane, a polyglycolic acid membrane or film.

This group includes for example the Skin²™ model ZK1100 and Dermagraft® and Transcyte® dermal models (Advanced Tissue Sciences);
  a cell culture-treated plastic (formation of a dermal sheet: Michel et al., *In Vitro Cell. Dev Biol.-Animal,* 35: 318-326, 1999);
  a gel or a membrane based on hyaluronic acid (Hyalograft® 3D—Fidia Advanced Biopolymers) and/or collagen (such as for example an equivalent dermis or collagen lattices) and/or fibronectin and/or fibrin; this group includes for example the Vitrix® dermal model (Organogenesis);
  an optionally surfaced porous matrix (for example an equivalent dermis), produced from collagen suitable for containing one or more glycosaminoglycans and/or optionally chitosan (EP0296078A1, WO 01/911821 and WO 01/92322).

This group also includes for example the Mimederm® dermal model (Coletica).

These matrix substrates comprise stromal cells, particularly fibroblasts.

Advantageously, said skin model is an epidermis model comprising a matrix substrate preferably selected from:
  an inert substrate selected from the group consisting of a semi-permeable synthetic membrane, in particular a semi-permeable nitrocellulose membrane, a semi-permeable nylon membrane, a Teflon membrane or sponge, a polycarbonate or polyethylene, polypropylene, semi-permeable polyethylene terephthalate (PET) membrane, an inorganic semi-permeable Anopore, cellulose acetate or ester (HATF) membrane, a semi-permeable Biopore-CM membrane, a semi-permeable polyester membrane;

this group includes the Reconstructed epidermis models (Skinethic®) and the EpiDerm® model (Mattek Corporation);
  a film or a membrane based on hyaluronic acid and/or collagen and/or fibronectin and/or fibrin.

In this group, particular mention may be made of the models: Laserskin® (Fidia Advanced Biopolymers), Episkin® (L'Oréal).

These models may be inoculated with fibroblasts in the dermal part.

These models, wherein fibroblasts may be optionally integrated, act as a substrate for keratinocyte inoculation and epidermis reconstruction. Advantageously, beside keratinocytes, pigment cells, immunocompetent cells, nerve cells are introduced; preferably, the immunocompetent cells are Langerhans cells.

Advantageously, said tissue model is a reconstructed skin or mucosal tissue model comprising a dermal or chorion matrix substrate, preferably selected from:
  an inert substrate selected from the group consisting of a semi-permeable synthetic membrane, in particular a semi-permeable nitrocellulose membrane, a semi-permeable nylon membrane, a Teflon membrane or sponge, a polycarbonate or polyethylene, polypropylene, semi-permeable polyethylene terephthalate (PET) membrane, an inorganic semi-permeable Anopore, cellulose acetate or ester (HATF) membrane, a semi-permeable Biopore-CM membrane, a semi-permeable polyester membrane, said inert substrate optionally containing stromal cells, particularly fibroblasts,
  a gel based on collagen and/or hyaluronic acid and/or fibronectin, and/or fibrin comprising stromal cells, particularly fibroblasts,
  an optionally surfaced porous matrix, produced from collagen suitable for containing one or more glycosaminoglycans and/or optionally chitosan, these porous matrixes incorporating stromal cells, particularly fibroblasts,
  a de-epidermized dermis or dead dermis, of human or animal origin.

In this group, particular mention may be made of the following models: Mimeskin (Coletica), EpidermFT™, Epi-Airway™, EpiOccular™ EpiOral™, EpiGingival™, EpiVaginal™ (MatTek corporation), Human Corneal Epithelium (HCE), Human Oral Epithelium (HOE), Human Gingival Epithelium (HGE), Human Vaginal Epithelium (HVE) (Skinethic®), Phenion® Full Thickness Skin Model (Phenion), Apligraf® (Organogenesis), ATS-2000 (CellSystems® Biotechnologie Vertrieb) and Skin™ (ZK1200-1300-2000 Advanced Tissue Science).

Furthermore, models specifically intended for tissue therapy are available which also may be used within the scope of the present invention. Mention may be made of the Epidex (Modex Thérapeutiques), Epibase® (Laboratoire Genévrier), Epicell™ (Genzyme), Autoderm™ and Transderm™ (Innogenetics) models.

The matrix substrate is then inoculated with keratinocytes to reconstruct the epidermis and eventually obtain a reconstructed skin.

Advantageously, the skin model used comprises a model wherein at least one complementary cell type has been incorporated, such as endothelial cells (EC) and/or immune cells such as lymphocytes, macrophages, mast cells, dendritic cells and/or adipose cells and/or skin appendages, such as hair on the body and head, sebaceous glands.

After the formulation of interest and the skin culture of the invention have been contacted, the reconstructed skin model thus treated may be exposed to urine.

The expression "expose the reconstructed skin model to urine", in the meaning of the invention, refers to any exposure or contacting of said reconstructed skin model with urine, whether natural or synthetic.

Thus, according to a preferred embodiment, exposure of said reconstructed skin model to urine according to the invention comprises or consists of exposure to natural urine, i.e. urine produced naturally by a human being. According to a more preferred embodiment, exposure of the reconstructed skin model to urine according to the invention comprises or consists of exposure to artificial or synthetic urine, i.e. urine the composition of which is determined and constant. According to an even more preferred embodiment, exposure of the reconstructed skin model to urine according to the invention comprises or consists of exposure to synthetic urine comprising urea, creatinine, ammonium acetate and citric acid. Preferentially, the pH of the synthetic urine to which the skin culture is thus exposed is between 6 and 10 and more preferentially between 7 and 9; still more preferentially, the pH of the synthetic urine according to the invention is equal to 8.

After having exposed the reconstructed skin model of the invention to urine, persons skilled in the art will be able to proceed to measuring the expression level of the biological markers of the invention.

The term "biological marker" in the meaning of the present application refers to a characteristic which is objectively measured and evaluated as an indicator of normal biological processes, pathogenic processes, or pharmacological responses to a therapeutic intervention. A biological marker thus refers to a whole range of various substances and parameters. For example, a biological marker may be a substance the detection of which indicates a particular diseased state (for example the presence of activated protein C as a marker of infection), or on the contrary a substance the detection of which indicates a specific physiological state. The biological marker according to the invention is preferentially a gene, gene products such as transcripts thereof and peptides derived from transcripts thereof, a lipid, a sugar or a metabolite.

According to an embodiment of the present invention, the biological marker is a gene, gene products such as transcripts or peptides, a lipid, a sugar or a metabolite the changes in expression of which, in particular the expression level, correlate with a physiological state of children's skin. According to a particular embodiment, the biological marker is a peptide having an enzymatic activity.

Persons skilled in the art seeking to determine the class to which a genetic or protein marker belongs can easily consult the relevant scientific literature or refer to public databases such as, for example, those contained in the National Center for Biotechnology Information website (http://www.ncbi.nlm.nih.gov/guide/).

The Inventors particularly selected markers the variation of the expression level of which varies after exposure to urine in a surprising and unexpected manner in children. The selected markers thus have a particular advantage within the scope of the method of the invention, insofar as their expression level is measured on a skin model reproducing the characteristics of children's skin.

The Inventors thus showed that markers of inflammation are particularly expressed after children's skin was treated with urine. Inflammation is a normal defense reaction of the body, but it can contribute to reducing the skin's integrity. Moreover, the Inventors showed that at same time, the expression of barrier markers decreases.

Finally, stem cell markers, and consequently the skin's capacity of renewal, are also affected. On the other hand, contacting the skin with a formulation active against the effects of urine makes it possible to prevent and correct the variations of expression of said markers, which underlines the relevance thereof.

The biological marker of the invention is thus advantageously a marker selected from the group of skin inflammation markers, barrier function markers and markers preferentially expressed in stem cells.

The expression "skin inflammation markers", in the meaning of the invention, refers to markers the variation of expression of which correlates with skin inflammation.

The term "inflammation" according to the invention refers to the set of defense reaction mechanisms by which the body recognizes, destroys and eliminates all substances foreign to it. "Skin inflammation" corresponds more particularly to an immune system reaction to an attack on the skin, such as an environmental attack, optionally causing a wound, even vascular damage as the case may be. Skin inflammation may appear as an erythema, characterized by redness associated with local vasodilatation, an edema, characterized by swelling, and a sensation of heat. Moreover, skin inflammation is accompanied by a variation of expression level or concentration of genetic or protein markers well-known to persons skilled in the art, who can refer, for example, to Vahlquist (*Acta Derm Venereal;* 80: 161; 2000).

The triggering and the continuation of the inflammation, and the diffusion thereof from the initial source, require factors which are synthesized locally or which are in the inactive precursor state in the circulation. Specific processes in the inflammation reaction can be differentiated according to the mediator type synthesized. Thus, the skin inflammation according to the invention includes at least three distinct processes, protein inflammation, lipid inflammation and neurogenic inflammation.

The term "protein inflammation" as used herein refers to the production, in response to an external attack, of protein inflammatory mediators, such as the cytokines IL-1, IL-2, IL-6, IL8 and TNFα, the complement system, or proteins involved in coagulation, as the case may be. The term "lipid inflammation" as used herein refers to the production to said external attack of lipid mediators, in particular prostaglandins and leukotrienes, both synthesized from arachidonic acid, as well as activation of the enzymes responsible for this production (Shimizu, *Annu Rev Pharmacol Toxicol.*, 49: 123-150, 2009). The protein and lipid mediators thus produced will induce a reaction cascade within the skin involving other inflammatory cells, in particular immune and vascular cells. The clinical result is expressed particularly by redness or edema.

In response to an external attack, the neurosensory system had to be stimulated and associated with the inflammatory reaction implementing then other cellular actors such as nerves (or nerve endings) and cells such as mast cells. The term "neurogenic inflammation" as used herein refers to the release by nerve endings, in response to an external attack, of specific mediators, in particular neuropeptides (in particular tachykinins including substance P, and Calcitonin Gene-Related Peptide or CGRP); also participating in the neurogenic inflammation according to the invention is the activity of particular receptors such as the substance P receptor or the receptor TRPV1. Neurogenic inflammation most often results in a sensation of pain and/or discomfort and/or of itching (pruritus).

The skin inflammation marker according to the invention is preferably selected from protein inflammation markers, lipid inflammation markers and neurogenic inflammation markers.

Preferentially, the protein inflammation marker is selected from the group consisting of interleukins, preferably IL1α and IL8. Human interleukin IL1α has a protein sequence represented by the sequence of NCBI reference: NP_000566. This protein is encoded by the human IL1A gene (NCBI reference: Gene ID: 3552), the sequence of which corresponds to NCBI reference: NM_000575. The protein sequence of human interleukin IL-8 corresponds to the sequence of NCBI reference: NP_000575. This protein is encoded by the human IL8 gene (NCBI reference: Gene ID: 3576). The sequence thereof is accessible under NCBI reference: NM_000584.

The lipid inflammation marker is advantageously selected from prostaglandins, including in particular prostaglandin E2, and enzymes of the synthesis thereof from arachidonic acid, in particular PTGS2.

Prostaglandin E2 (PGE2) is a well-known arachidonic acid derivative obtained by the action of cyclooxygenase. Two isoforms of cyclooxygenase (COX) exist: cyclooxygenase 1, which is constitutive in tissues, and cyclooxygenase 2, which is induced by inflammatory phenomena. Proinflammatory stimulation (trauma, cytokines, etc.) thus lead to the synthesis of PGE 2, which is responsible for vasodilatation (generating redness and edema), sensitization of nociceptors to bradykinin and histamine (responsible for pain) and fever (with cytokines 11 and IL6).

The enzyme cyclooxygenase 2, also called prostaglandin-endoperoxide synthase (PTGS), is encoded by the human PTGS2 gene (NCBI reference: Gene ID: 5743). The sequence of this gene is available under the NCBI reference: NM_000963 and the protein sequence under NCBI reference: NP_000954.

Preferably, the marker of neurogenic inflammation is selected from neuropeptides and neuropeptide receptors, in particular the receptors TRPV1 and SPR. The receptor TRPV1 (Transient Receptor Potential Vanilloid 1) is a cation-channel type membrane protein of the TRP family having the sequence of NCBI reference: NP_061197. In the skin, TRPV1 is expressed by keratinocytes, mast cells and nerve fibers. In response to an aggressor, TRPV1 activation leads to the production of cytokines and neuropeptides and is an actor in neurogenic inflammation. The gene encoding receptor TRPV1 is the TRPV1 gene (NCBI reference: Gene ID: 7442), the sequence of which has the NCBI reference: NM_018727.

Substance P receptor (SPR; also known as neurokinin 1 receptor, NK1R, or tachykinin receptor 1, TACR1) is a G protein-coupled receptor (GPCR) which transmits the signal of substance P (SP) and other tachykinins. It is encoded by the human TACR1 gene, the sequence of which has the NCBI reference: NM_001058. Its peptide sequence is the sequence of NCBI reference: NP_001049.

According to the invention, the skin inflammation marker is thus preferably selected from the group consisting of IL1a, IL8, PTGS2, PGE2, TRPV1 and SPR.

The present Inventors further showed that urine induces a reduction in the expression of barrier function markers and markers preferentially expressed in stem cells.

The "barrier markers" according to the invention comprise markers which are expressed specifically in the outermost layers of the epidermis and which participate in the barrier function.

As persons skilled in the art well know, the main function of the skin is to establish a protective barrier against environmental attacks while allowing certain exchanges between the internal environment and the external environment. This barrier function is chiefly provided by the stratum corneum of the epidermis. Intercellular lipids and corneodesmosomes, and the cornified envelope of corneocytes, are the key components.

However, beneath the stratum corneum, tight junctions constitute a second line of the barrier function. These junctions constitute in the stratum granulosum a selective paracellular diffusion barrier preventing the penetration of harmful molecules. Tight junctions are made up of various transmembrane proteins such as in particular claudins, occludin and ZO1.

The barrier functions provided by the stratum corneum and the tight junctions are closely linked. Indeed, the alteration of one can influence the formation of the other.

Preferentially, the barrier function markers according to the invention are markers expressed in the stratum corneum or markers expressed in the tight junctions of the stratum granulosum. In a more preferential embodiment, said epidermal barrier marker is selected from the group consisting of CDSN (corneodesmosin), IVL (involucrin), SMPD (sphingomyelinase or sphingomyelin diesterase), and CLDN1 (claudin 1).

The corneodesmosome is the only junction structure of the corneal layer, which underlines the importance of this structure for maintaining corneal layer integrity. One of the principal components of the corneodesmosome is corneodesmosin. It is the only specific protein of the corneodesmosome: it thus plays an essential role within this junction structure. Its sequence corresponds to that under reference NP_001255. The CDSN gene (NCBI reference: Gene ID: 1041) encodes corneodesmosin and has the sequence of reference NM_001264.

Involucrin, having sequence NP_005538 and encoded by the IVL gene (NCBI reference: Gene ID: 3713), which itself has sequence NM_005547, participates in the formation of the cornified envelope of corneocytes.

Sphingomyelinase (SMase) or sphingomyelin diesterase is a hydrolase involved in sphingolipid metabolism. It cleaves sphingomyelins into phosphocholine and ceramides 2 and 5, which are part the intercellular lipid matrix which ensures the watertightness of the corneal layer. Sphingomyelinase is a protein the sequence of which is represented by NCBI reference: NP_000534. The gene encoding this enzyme is the SMPD gene (NCBI reference: Gene ID: 6609) having the sequence corresponding to reference NM_000543.

Tight junctions represent one mode of cell adhesion, in epithelial tissues. They block the circulation of fluids between cells and thus ensure watertightness between two tissue compartments. They are located at the apex of epithelial cells where they form a continuous band around which watertightness is ensured. The CLDN 1 gene (NCBI reference: Gene ID: 9076) encodes the claudin 1 protein which is one of the most important components of tight junctions. This protein has a sequence corresponding to that of NCBI reference NP_066924. The CLDN1 gene sequence is accessible under reference NM_021101.

The expression "markers preferentially expressed in stem cells" according to the invention refers to the markers, and more specifically to the genes and proteins, which are specifically present in epidermal stem cells.

The expression "stem cell of the epidermis" or "epidermal stem cell", in the meaning of the present invention, refers to an epidermal cell capable of long-term renewal. The epidermal stem cells of the invention comprise, among others, follicular stem cells, sebaceous stem cells and basal stem cells, the latter also being called interfollicular epidermal stem cells. The terms "follicular stem cells", "sebaceous stem cells" and "basal stem cells", in the meaning of the invention, refer to stem cells located in the region of the hair follicle bulge, in sebaceous glands and in the basal layer of the epidermis, respectively. In a preferential embodiment of the invention, the epidermal stem cells of the invention are basal stem cells.

More precisely, the term "epidermal stem cell", in the meaning of the present invention, refers to a cell bestowed with a high potential for long-term renewal. The term "potential for renewal" as used herein refers to the capacity to undergo at least one cell division cycle. A "high potential for long-term renewal" thus represents a cell's capacity to enter several successive cell division cycles. It is well-known that cells differentiated from the skin are not capable of carrying out several successive divisions (Fortunel and Martin, *J Soc Biol,* 202(1): 55-65, 2008). It is understood herein that "successive" does not mean "consecutive" and that there may be periods during which a stem cell according to the invention remains quiescent without however losing its high potential for long-term renewal.

Conservation of a high potential for long-term renewal is expressed by asymmetrical division producing two different cells. The first daughter cell is a stem cell identical to the mother stem cell, while the second is a transit amplifying cell that divides in a limited manner over a short period of time and then enters the differentiation process. Advantageously, the epidermal stem cells of the invention thus are further capable of generating at least one type of epidermal cell by differentiation. In other words, the transit amplifying cell is capable of giving rise to at least one type of epidermal type by differentiation. Preferentially, said epidermal cell is a keratinocyte. More preferentially, the transit amplifying cell is capable of giving rise to all the types of epidermal cells by differentiation.

Preferentially, the markers expressed in stem cells are markers that participate in the functions and the protection of stem cells. Mention may be made, for example, of the markers ΔNp63, BIRC5 (survivin), FN1 (fibronectin 1), MCSP (melanoma-associated chondroitin sulfate proteoglycan), LRIG1 (leucine-rich repeats and immunoglobulin-like domains protein 1), GJA1 (connexin 43), NID1 (nidogen 1), KRT15 (keratin 15), KRT19 (keratin 19), EGFR (epidermal growth factor receptor), CD71 (transferrin receptor), DSG3 (desmoglein 3), ITGB1BP1 (integrin beta1 binding protein), ITGA6 (integrin alpha 6), ITGB1 (integrin beta1) and ITGB4 (integrin beta 4) or markers involved in the signaling and regulation of stem cell activity such as Wnt/beta catenin, sonic hedgehog (SHH), NOTCH1 (notch homolog 1, translocation-associated). ΔNp63 and survivin are markers of resistance to apoptosis, thus having a role in stem cell survival. Cytokeratins 15 and 19 are positive stem cell markers, cytokeratin 15 being a marker of their survival. MCSP colocalizes with integrins in cells that do not divide, whereas integrin beta1 (marker of basal membrane adhesion to the extracellular matrix) and integrin alpha 6 (constituting hemidesmosomes, marker of keratinocytes binding together) are surface proteins that take part in intercellular communication, regulating the differentiation/proliferation processes as well as interaction with the niche. Transferrin receptor CD71 is a known surface marker for stem cells which is used to isolate, in a population of integrin alpha6-positive cells, cells with high clonogenic capacity. Finally, Lrig1 is an epidermal growth factor receptor (EGFR) antagonist, thus maintaining quiescent stem cells, whereas receptor EGFR, which is a marker whose absence characterizes stem cells, in contrast leads the cells down the proliferation pathway.

Preferentially, the marker preferentially expressed in the stem cells of the invention is selected from the group consisting of the markers KRT19 (keratin 19), BIRC5 (survivin), LRIG1 (leucine-rich repeats and immunoglobulin-like domains protein 1), ITGA6 (integrin alpha 6), ITGB1 (integrin beta1) and ITGB4 (integrin beta 4). These markers are well-known to persons skilled in the art. The KRT19 (NCBI reference: Gene ID: 3880), BIRC5 (NCBI reference: Gene ID: 332), LRIG1 (NCBI reference: Gene ID: 26018), ITGA6 (NCBI reference: Gene ID: 3655), ITGB1 (NCBI reference: Gene ID: 3688) and ITGB4 (NCBI reference: Gene ID: 3691) genes thus correspond to the sequences represented by the following Genbank accession numbers: NM_002276, NM_001012270, NM_015541, NM_000210, NM_002211 and NM_000213, respectively. The proteins keratin 19, survivin, leucine-rich repeats and immunoglobulin-like domains protein 1, integrin alpha 6, integrin beta1 and integrin beta 4 correspond, in turn, to the sequences represented by the following Genbank accession numbers: NP_002267, NP_001012270, NP_056356, NP_000201, NP_002202 and NP_000204, respectively.

It will be further evident to persons skilled in the art that the method of the invention will allow an evaluation of the efficacy of the formulation or the active agent which will be all the more complete when a large number of markers of different types are used.

According to a preferred embodiment, the method of the invention comprises a step c) of measuring the expression level of a combination of biological markers. Said combination according to the invention comprises or consists of:
- at least one skin inflammation marker and at least one barrier marker as defined above; or
- at least one skin inflammation marker and at least one marker preferentially expressed in stem cells, as defined above; or
- at least one barrier marker and at least one marker preferentially expressed in stem cells, as defined above.

In a more preferential embodiment, said combination comprises at least one skin inflammation marker and at least one barrier marker and at least one marker preferentially expressed in stem cells, as defined above.

The use of combinations of markers comprising at least one marker of each of the various types indicated above is particularly advantageous.

For each of these markers, the term "expression level" refers to the cellular concentration of said marker. Thus the expression level of prostaglandin E2 corresponds to the concentration of said lipid in the cell. If the marker is a gene, the "expression level" in the meaning of the invention corresponds to the cellular concentration of at least one product of the gene of said marker. More precisely, the expression level of said biological marker corresponds to the quantity or to the cellular concentration of the transcript of said gene or of the protein derived from said transcript. According to a preferred embodiment, the expression level of said biological marker corresponds to the quantity or to the cellular concentration of the transcript of said gene. According to another embodiment, the expression level of said biological marker corresponds to the quantity or to the cellular concentration of the protein derived from said transcript.

The expression "measuring the expression level of a combination of biological markers", in the meaning of the present application, refers to measuring the expression level of each marker of the combination. The expression of a gene may be measured for example at the nucleotide level, by measuring the quantity of transcripts of said gene, and also may be measured for example at the peptide level, by measuring for example the quantity of proteins derived from said transcript. Thus, the expression "measuring the expression level of said gene" in the meaning of the invention refers to measuring the quantity of the gene product in its peptide form or its nucleotide form.

Generally, the expression of the biological marker according to the invention will be detected in vitro from the reconstructed skin model.

In a particular embodiment, the method of the invention may comprise one or more intermediate steps between obtaining the reconstructed skin model and measuring the expression of the biological marker, said steps corresponding to extracting from said reconstructed skin model a lipid sample, an mRNA (or corresponding cDNA) sample or a protein sample. Said sample may then be used directly to measure the expression of the marker. The preparation or extraction of mRNA (and the reverse transcription thereof into cDNA), proteins or lipids from a cellular sample is a routine procedure well-known to persons skilled in the art.

With regard to lipid mediators such as prostaglandin E, it may not even be necessary to prepare a lipid sample. Indeed, this mediator is secreted in the culture medium. It is then easy for persons skilled in the art to assay prostaglandin E2 from said culture medium. Several methods for assaying and quantifying prostaglandin E2 have thus been described in the art, including in particular ELISA methods. Such a method is thus detailed in the experimental section of the present application and persons skilled in the art can refer thereto. It should also be noted that kits are commercially available for assaying prostaglandin E2 (for example, from CissBio Assays or from Pierce).

Once a sample of mRNA (or corresponding cDNA) or protein is obtained, the expression of the marker, in terms of either mRNA (i.e. in all the mRNA or cDNA present in the sample) or proteins (i.e. in all the proteins present in the sample), can be measured. The method used to that end thus depends on the type of transformation (mRNA, cDNA or protein) and on the type of sample available.

When the expression of the marker is measured at the mRNA (or the corresponding cDNA) level, any technology commonly used by persons skilled in the art may be used. These technologies for analyzing levels of gene expression, such as transcriptome analysis, for example, include well-known methods such as PCR (polymerase chain reaction, if starting with DNA), RT-PCR (reverse transcription-PCR, if starting with RNA) and quantitative RT-PCR, or nucleic acid chips (including DNA chips and oligonucleotide chips) for a higher throughput.

The term "nucleic acid chips" as used herein refers to several different nucleic acid probes attached to a substrate, which may be a microchip, a glass slide or a microsphere-size bead. The microchip may be composed of polymers, plastics, resins, polysaccharides, silica or a material containing silica, carbon, metals, inorganic glass or nitrocellulose.

The probes may be nucleic acids such as cDNA (cDNA chips), mRNA (mRNA chips) or oligonucleotides (oligonucleotide chips), said oligonucleotides typically having a length of between roughly 25 and 60 nucleotides.

To determine the expression profile of a particular gene, a nucleic acid corresponding to all or part of said gene is marked and then contacted with the chip under hybridization conditions, leading to the formation of complexes between said marked target nucleic acids and probes complementary to this nucleic acid attached to the surface of the chip. The presence of the marked hybrid complexes is then detected.

These technologies make it possible to follow the expression level of one gene in particular or several genes, and even of all the genes of the genome (full genome or full transcriptome) in a biological sample (cells, tissues, etc.). These technologies are used routinely by persons skilled in the art and thus it is not necessary to detail them herein. Examples of implementations of the invention based on analysis of gene expression (cDNA chips) and on quantitative PCR are described in the experimental section.

Alternatively, it is possible to use any current or future technology making it possible to determine the expression of genes on the basis of the quantity of mRNA in the sample. For example, persons skilled in the art can measure the expression of a gene by hybridization with a marked nucleic acid probe, such as, for example, with a Northern blot (for mRNA) or a Southern blot (for cDNA), but also by techniques such as the serial analysis of gene expression (SAGE) method and derivatives thereof, such as LongSAGE, SuperSAGE, DeepSAGE, etc. It is also possible to use tissue chips (also known as tissue microarrays, or TMAs). The tests commonly employed with tissue chips include immunohistochemistry and fluorescent in situ hybridization. For the analysis of mRNA levels, tissue chips may be coupled with fluorescent in situ hybridization. Finally, it is possible to use massively parallel sequencing to determine the quantity of mRNA in the sample (RNA-Seq, or whole transcriptome shotgun sequencing). For that purpose, several methods of massively parallel sequencing are available. Such methods are described in, for example, U.S. Pat. Nos. 4,882,127; 4,849,077; 7,556,922; 6,723,513; WO 03/066896; WO 2007/111924; US 2008/0020392; WO 2006/084132; US 2009/0186349; US 2009/0181860; US 2009/0181385; US 2006/0275782; EP-B1-1141399; Shendure Et Ji, *Nat Biotechnol.*, 26(10): 1135-45. 2008; Pihlak et al., *Nat Biotechnol.*, 26(6): 676-684, 2008; Fuller et al., *Nature Biotechnol.*, 27(11): 1013-1023, 2009; Mardis, *Genome Med.*, 1(4): 40, 2009; Metzker, *Nature Rev. Genet.*, 11(1): 31-46, 2010.

When the expression of the marker is measured at the protein level, it is possible to employ specific antibodies, in particular in well-known technologies such as immunoprecipitation, immunohistology, Western blot, dot blot, ELISA or ELISPOT, protein chips, antibody chips, or tissue chips coupled with immunohistochemistry. Other techniques that may be used include FRET or BRET techniques, methods of microscopy or histochemistry, notably including methods of confocal microscopy and electron microscopy, methods based on the use of one or more excitation wavelengths and a suitable optical method, such as an electrochemical method (voltammetry and amperometry techniques), atomic force microscopy, and radio frequency methods, such as multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, etc.), flow cytometry, radioisotope or magnetic resonance imaging, analysis by polyacrylamide gel electrophoresis (SDS-PAGE), HPLC-mass spectrometry and liquid chromatography-mass spectrophotometry/mass spectrometry (LC-MS/MS). All of these techniques are well-known to the skilled person and it is not necessary to detail them herein.

The expression "a reference expression level of a biological marker", in the meaning of the present application, refers to any expression level of said marker used as a reference. For example, a reference expression level may be obtained by measuring the expression level of the marker of interest in a children's skin model, under particular conditions. Persons skilled in the art will be able to choose these particular conditions as a function of intended purpose when implementing the invention.

For example, in a preferred embodiment, the reference expression level of a biological marker is the expression level of said marker obtained in a children's skin model not treated with the formulation or active agent of interest, and exposed to UV.

According to another embodiment, the reference expression level of a biological marker is the expression level of said marker obtained in a children's skin model, contacted with a reference formulation or active agent, and exposed to urine.

When the reference expression level is an expression level obtained in a skin model exposed to urine, persons skilled in the art will easily understand that the conditions of urine exposure for the skin model used in the method of the invention and for the model used to obtain a reference expression level are preferentially the same. Thus, preferentially, the composition of the artificial urine used, and the exposure time used in the method of the invention and for the model used to obtain a reference expression level, are preferentially the same.

For example, persons skilled in the art can use as a reference formulation any formulation known in the prior art for its effect in preventing the harmful effects of urine on the skin.

Preferentially, the reference formulation is selected from a continuous oil phase emulsion diaper-change formula, a continuous fatty phase ointment diaper-change formula, an aqueous paste diaper-change formula, a continuous oil phase emulsion diaper-change formula, a diaper-change liniment and diaper-change wipes. More preferentially, the continuous oil phase emulsion diaper-change formula corresponds to the formulation of Table 1, the continuous fatty phase ointment diaper-change formula to that of Table 2, the aqueous paste diaper-change formula to that of Table 3, the continuous oil phase emulsion diaper-change formula to that of Table 4, the diaper-change liniment to that of Table 5 and the diaper-change wipes to that of Table 6.

TABLE 1

Diaper-change formula P1 - continuous oil phase emulsion

| RAW MATERIAL | % |
|---|---|
| WATER | q.s. |
| ZINC OXIDE | 5 to 20% |
| CAPRYLIC/CAPRIC TRIGLYCERIDE | 5 to 20% |
| COCO-CAPRYLATE/CAPRATE | 1 to 10% |
| POLYGLYCERYL-2-DIPOLYHYDROXYSTEARATE | 1 to 10% |
| GLYCERIN | 1 to 10% |

TABLE 1-continued

Diaper-change formula P1 - continuous oil phase emulsion

| RAW MATERIAL | % |
|---|---|
| WAXES | 1 to 5% |
| *PERSEA GRATISSIMA* OIL | 1 to 5% |
| POLYGLYCERYL-3 DIISOSTEARATE | 1 to 5% |
| MAGNESIUM SULFATE | 0 to 2% |
| STEARALKONIUM HECTORITE | 0 to 2% |
| PRESERVATIVES | 0 to 2% |
| *PERSEA GRATISSIMA* FRUIT EXTRACT/AVOCADO PERSEOSE | 0 to 5% |
| *HELIANTHUS ANNUUS* SEED OIL UNSAPONIFIABLES | 0 to 5% |
| UNDECYL DIMETHYL OXAZOLINE | 0 to 5% |
| ETHYL LINOLEATE | 0 to 5% |
| CAPRYLOYL GLYCINE | 0 to 5% |

TABLE 2

Diaper-change formula P2 - continuous fatty phase ointment

| RAW MATERIAL | % |
|---|---|
| ZINC OXIDE | 10 to 30% |
| FISH LIVER OIL/VITAMIN B5 | 10 to 30% |
| LANOLIN | 10 to 30% |
| PETROLEUM JELLY | q.s. |
| ANTIOXIDANT | 0 to 2% |
| FRAGRANCE/ESSENTIAL OIL | 0 to 2% |

TABLE 3

Diaper-change formula P3 - aqueous paste

| RAW MATERIAL | % |
|---|---|
| VITAMIN B5 | 1 to 10% |
| ZINC OXIDE | 1 to 20% |
| TITANIUM DIOXIDE | 1 to 5% |
| MINERAL FILLER (KAOLIN, TALC, SILICA) | 1 to 20% |
| ACTIVE AGENT | 1 to 5% |
| PRESERVATIVES | 0 to 2% |
| WATER | q.s. |
| GLYCERIN | 1 to 10% |
| SEQUESTRANT | 1 to 5% |

TABLE 4

Diaper-change formula - continuous oil phase emulsion

| RAW MATERIAL | % |
|---|---|
| VITAMIN B5 | 1 to 10% |
| CETYL ALCOHOL | 10 to 30% |
| STEARYL ALCOHOL | 10 to 30% |
| PETROLEUM JELLY/PARAFFIN | 1 to 10% |
| ANTIOXIDANT | 0 to 2% |
| PLANT OIL | 1 to 10% |
| WAX | 1 to 10% |
| WATER | q.s. |

TABLE 5

Diaper-change liniment

| RAW MATERIAL | % |
|---|---|
| PLANT OIL | 20 to 50% |
| WATER + CALCIUM HYDROXIDE | q.s. |
| STABILIZER | 1 to 5% |

TABLE 5-continued

Diaper-change liniment

| RAW MATERIAL | % |
|---|---|
| PERSEA GRATISSIMA FRUIT EXTRACT/AVOCADO PERSEOSE | 0 to 5% |
| HELIANTHUS ANNUUS SEED OIL UNSAPONIFIABLES | 0 to 5% |
| UNDECYL DIMETHYL OXAZOLINE | 0 to 5% |
| ETHYL LINOLEATE | 0 to 5% |
| CAPRYLOYL GLYCINE | 0 to 5% |
| PRESERVATIVES | 0 to 2% |
| ANTIOXIDANT | 0 to 2% |

TABLE 6

Diaper-change wipes

| RAW MATERIAL | % |
|---|---|
| WATER | q.s. |
| GLYCERIN | 0 to 2% |
| PEG-40 HYDROGENATED CASTOR OIL | 0 to 2% |
| FRAGRANCE | 0 to 2% |
| PRESERVATIVES | 0 to 2% |
| PERSEA GRATISSIMA FRUIT EXTRACT/AVOCADO PERSEOSE | 0 to 5% |
| HELIANTHUS ANNUUS SEED OIL UNSAPONIFIABLES | 0 to 5% |
| UNDECYL DIMETHYL OXAZOLINE | 0 to 5% |
| ETHYL LINOLEATE | 0 to 5% |
| CAPRYLOYL GLYCINE | 0 to 5% |
| pH ADJUSTER | 0 to 1% |

According to another preferred embodiment, the reference expression level of a biological marker is the expression level of said marker obtained in a skin model obtained from a skin sample from a child, said model not being treated with the formulation or active agent of interest, and not exposed to urine.

According to another preferred embodiment, the reference expression level of a biological marker is the expression level of said marker obtained in a skin model obtained from a skin sample from a child, said model not being treated with the formulation or active agent of interest, but being exposed to urine.

According to another embodiment, the reference expression level of a biological marker is the expression level of said marker obtained in a skin model obtained from a skin sample from a child, treated with the formulation or active agent of interest, and not exposed to urine.

Persons skilled in the art will further easily understand that the comparison of step d) is preferably carried out between the measurements of expression levels obtained for skin models obtained from skin samples from children, or from similar or even identical histological structures. The expression "similar histological structures", in the meaning of the present application, means that the relative proportions of cell types comprised in the compared skin models are similar. Thus, it is preferable that the relative proportions of cell types comprised in the skin model of step a) do not differ by more than 5% from the relative proportions of cell types comprised in the skin model used to obtain the reference expression level of step d). The expression "relative proportion of a cell type", in the meaning of the present application, refers to the ratio of the number of cells corresponding to this cell type to the total number of cells comprised in the skin model. Thus, for example, it is preferable that the proportion of keratinocytes to the total number of cells in the skin model of step a) does not differ by more than 5% from the proportion of keratinocytes to the total number of cells in the skin model used to obtain the reference expression level of step d). The expression "identical histological structures", in the meaning of the present application, means that the relative proportions of cell types comprised in the compared skin models are identical. In the meaning of the present invention, the relative proportions of cell types comprised in the nipple skin model of step a) are identical to the relative proportions of cell types comprised in the skin model used to obtain the reference expression level of step d) when they do not differ by more than 0.1%. Advantageously, the proportion of keratinocytes to the total number of cells in the skin model of step a) does not differ by more than 0.1% from the proportion of keratinocytes to the total number of cells in the skin model used to obtain the reference expression level of step d).

Persons skilled in the art will also easily understand that the comparison of step d) is preferably carried out between the measurements of expression levels obtained for skin models which are of similar, or even identical, size, volume or weight. Thus, it is preferable that the size, the volume or the weight of the skin model of step a) does not differ by more than 5% from the size, the volume or the weight of the skin model used to obtain the reference expression level of step d). More preferentially, the size, the volume and the weight of the skin model of step a) do not differ by more than 5% from the size, the volume and the weight of the skin model used to obtain the reference expression level of step c). Even more preferentially, the size, the volume and the weight of the skin model of step a) do not differ by more than 0.1% from the size, the volume and the weight of the skin model used to obtain the reference expression level of step d).

Alternatively, if the skin models differ by more than 5% in terms of size, volume and weight, persons skilled in the art will be able to normalize the level obtained in step c) and the reference level of step d) using a normalization factor.

This normalization factor, for example, could be a directly accessible physical marker such as the mass of the cells of the sample, or the mass of a cellular component, such as the mass of cellular DNA or the mass of cellular protein.

It also may be advantageous to use as the normalization factor the expression level of a gene which is expressed at the same level in all, or nearly all, of the body's cells. In other words, according to a particular embodiment of the present invention, the expression level of a housekeeping gene is used as the normalization factor. According to another embodiment, the level obtained in step c) and the reference level of step d) are normalized using the expression level not of housekeeping genes but of the proteins they encode. A housekeeping gene is a gene expressed in all cell types which encodes a protein having a basic function necessary for survival of all cell types. A list of human housekeeping genes can be found in Eisenberg et al. (*Trends in Genet*, 19: 362-365, 2003). The housekeeping genes according to the invention include for example the following genes: B2M, TFRC, YWHAZ, RPLO, 18S, GUSB, UBC, TBP, GAPDH, PPIA, POLR2A, ACTB, PGK1, HPRT1, IP08 and HMBS.

Persons skilled in the art will thus be able to easily evaluate the efficacy of the formulation of interest as a function of the comparison in step d).

According to another aspect, the invention has as an object a kit for implementing a method according to the invention, comprising the means necessary for measuring the expression level of at least one marker selected from skin inflammation markers, barrier function markers and markers preferentially expressed in stem cells. Preferably, the skin inflammation marker is selected from prostaglandin E2, PTGS2, IL-1α, IL-8, TRPV1 and SPR, the barrier function marker is selected from CNDSM, IVL, SMPD and CLDN1, and the marker preferentially expressed in stem cells is selected from KRT19, BIRC5, LRIG1, ITGA6, ITGB1 and ITGB4.

According to a particular embodiment, the kit according to the invention further comprises the means necessary for measuring the expression level of a combination of biological markers selected from the group comprising or consisting of:
- at least one skin inflammation marker and at least one barrier marker as defined above; or
- at least one skin inflammation marker and at least one marker preferentially expressed in stem cells, as defined above; or
- at least one barrier marker and at least one marker preferentially expressed in stem cells, as defined above.

In a more preferential embodiment, said combination comprises at least one skin inflammation marker and at least one barrier marker and at least one marker preferentially expressed in stem cells, as defined above.

The following examples are provided for illustration purposes and unless otherwise indicated are not intended to be limiting.

EXAMPLES

1. Effect of Urine on Reconstructed Epidermises of 1-Year-Old Infants—Model Set-Up 1.1. Introduction Diaper rash or irritative diaper dermatitis affects more than 35% of infants with a peak frequency around 10-12 months of age. Our research program on children's skin, centered on the epidermis, made it possible to show that:

Infants' skin is more fragile, and it less effectively fulfills its barrier role against external attacks and infections. The barrier being in the process of being built, it mobilizes its stock of stem cells (abundantly present at birth), thus making it more vulnerable. Finally, infants' skin has an inflammatory potential which only needs to be developed.

In the buttocks area, beneath the diaper, the damp atmosphere and occlusion quickly change these parameters toward more fragility, more inflammation and higher pH, which creates an imbalance. Moreover, in this context, extended contact with urine and stools (exogenous factors) can cause redness and pain, clinical signs of diaper rash.

Thus, associated with the known exogenous factors, these discoveries make it possible to clarify the mechanisms and factors which trigger diaper rash, namely an alteration of the barrier with an in-demand and vulnerable stock of stem cells and a strong inflammatory response.

To go further in understanding the action mechanisms and to be able to have a model for evaluating cosmetic diaper-change products, we developed a model which minimizes the harmful effects of urine on epidermises of 1-year-old infants (peak appearance of diaper rash) and studied the parameters found modulated thereby by analyzing the markers of various inflammation pathways, barrier function markers and stem cell markers.

To that end, epidermises were reconstructed with keratinocytes from a 1-year-old infant.

The effect of an artificial urine preparation was evaluated on these epidermises by analyzing the production of an inflammatory mediator (ELISA) and the gene expression (RT-qPCR) of the inflammation markers, barrier function markers and stem cell markers.

1.2. Material and Methods

The epidermises were produced with keratinocytes from a 1-year-old donor (foreskin removal) according to the model derived from the method of Poumay et al. (*Arch Dermatol Res;* 296: 203-211, 2004). After two days of submerged culture, the reconstructed human epidermises (RHEs) were cultured at the air/liquid interface for 10 days.

For each batch, at D10, the epidermises were incubated for 24 hours.

After incubation, the epidermises were treated (urine) or not (control) topically with an artificial urine preparation (composed of urea, creatinine, sodium chloride, ammonium acetate, citric acid, pH 8) then incubated overnight (16 hours).

All the experimental conditions were carried out with n=4.

Assay of the Inflammatory Mediator PGE2 in the Culture Supernatants

After incubation, the quantities of PGE2 present in the culture supernatants were measured using an ELISA kit according to the supplier's specifications.

Analysis of the Differential Expression of Genes

The expression of markers was evaluated by RT-qPCR on the messenger RNA extracted from the RHEs of each treatment.

The analysis of gene expression was carried out with n=2 using a PCR array containing genes of interest and two reference (housekeeping) genes. Total RNA from each sample was extracted using TriPure Isolation Reagent® according to the protocol recommended by the supplier. The quantity and the quality of the RNA were evaluated by capillary electrophoresis (Bioanalyzer, Agilent). Complementary DNA (cDNA) was synthesized by reverse transcription of the RNA in the presence of oligo(dT) and the enzyme "Transcriptor Reverse Transcriptase". The cDNA obtained was quantified by spectrophotometry, then the quantities of cDNA were adjusted.

The polymerase chain reactions were carried out by quantitative PCR with the "Light Cycler" system (Roche Molecular Systems Inc.) according to the procedure recommended by the supplier. The reaction mixture for each sample was: 10 ng/µl cDNA, primers for the various markers used, reaction mixture containing the enzyme taq DNA polymerase, the marker SYBR Green I (DNA intercalating agent) and $MgCl_2$.

The incorporation of fluorescence into the amplified DNA is measured continuously during the PCR cycles.

The quantitative analysis of the results is based on the collection of threshold cycles (Ct). The threshold cycle is the point at which the fluorescence emission signal is statistically and significantly higher than the background. The threshold cycle is directly correlated with the initial number of copies of target DNA.

For each sample, the expression level of the gene of interest is normalized by the expression level of the most stable reference gene, which under these experimental conditions is the GAPDH gene.

Table 7 lists the genes which were studied.

ΔCt is thus calculated:

$$\Delta Ct = Ct_{gene\ of\ interest} - Ct_{reference\ gene}$$

In a second step, the variation, as a function of the treatment, of the number of copies of the gene of interest was determined and ΔΔCt is calculated:

$$\Delta\Delta Ct = \Delta Ct_{control} - \Delta Ct_{urine}$$

Finally, relative quantity (RQ) is calculated: RQ=$(1+E)^{\Delta\Delta Ct}$.

Considering that E (efficacy) is equal to 1, relative quantity (RQ) is thus:

$$RQ=2^{\Delta\Delta Ct}$$

TABLE 7

Classification and name of genes

| Cluster name | Abbreviation | Gene name |
| --- | --- | --- |
| Housekeeping | RPS28 | Ribosomal protein 28S |
| | GAPDH | Glyceraldehyde-3-phosphate dehydrogenase |
| Inflammation | IL1A | Interleukin 1, alpha |
| | IL8 | Interleukin 8 |
| | TRPV1 | Transient receptor potential vanilloid, member 1 |
| | TACR1 or SPR | Tachykinin receptor 1 or Substance P receptor |
| | PTGS2 | Prostaglandin-endoperoxidase synthase 2 (prostaglandin G/H synthase and cyclooxygenase) |
| Epidermal differentiation, | IVL | Involucrin |
| | CDSN | Corneodesmosin |
| Barrier function | SMPD1 | Sphingomyelin phosphodiesterase 1, acid |
| | CLDN1 | Claudin 1 |
| Stem cells | KRT19 | Keratin 19 |
| | ITGB1 | Integrin, beta 1 |
| | ITGB4 | Integrin, beta 4 |
| | ITGA6 | Integrin, alpha 6 |
| | LRIG1 | Leucine-rich repeats and immunoglobulin-like domains 1 |
| | BIRC5 | Baculoviral IAP repeat-containing 5 or survivin |

1.3. Results and Conclusions 1.3.1. Inflammation

Infants' skin has a heightened inflammatory potential which in contact with "aggressor" agents will transform into a genuine inflammatory response causing redness and pain. In this context, exposure of the buttocks area to urine (and stools) in an occlusive environment will generate an inflammatory reaction involving three distinct and interconnected pathways: protein inflammation, lipid inflammation and neurogenic inflammation.

In the skin, the keratinocyte is one of the first cells taking part in initiation of the inflammatory reaction (early inflammation) in response to an environmental attack.

The "attacked" keratinocyte will then produce inflammatory mediator proteins (type cytokines IL1 and IL8) and/or lipids (like PGE2 and enzymes generating same from arachidonic acid such as PTGS2) which will induce a reaction cascade within the skin then involving other immune and vascular inflammatory cells. The clinical result is expressed as redness or edema.

In reaction to an attack, the neurosensory system can be stimulated and associated with the inflammatory reaction implementing then other cellular actors such as nerves (or nerve endings) and cells such as mast cells. This inflammatory reaction, described as neurogenic, also involves the production of specific mediators, which can be neuropeptides (such as substance P), and also receptors such as the substance P receptor and the receptor TRPV1*, in particular. The result is a sensation of pain and/or discomfort and/or itching (pruritus).

*The receptor or nociceptor TRPV1 (Transient Receptor Potential Vanilloid 1) is a cation-channel type membrane protein of the TRP family. In the skin, TRPV1 is expressed by keratinocytes, mast cells and nerve fibers. In response to an aggressor, TRPV1 activation leads to the production of cytokines and neuropeptides and is an actor of neurogenic inflammation.

Treating the reconstructed epidermises with the artificial urine preparation induced strong production of the lipid mediator of inflammation, PGE2 (FIG. 1).

Figure 4:
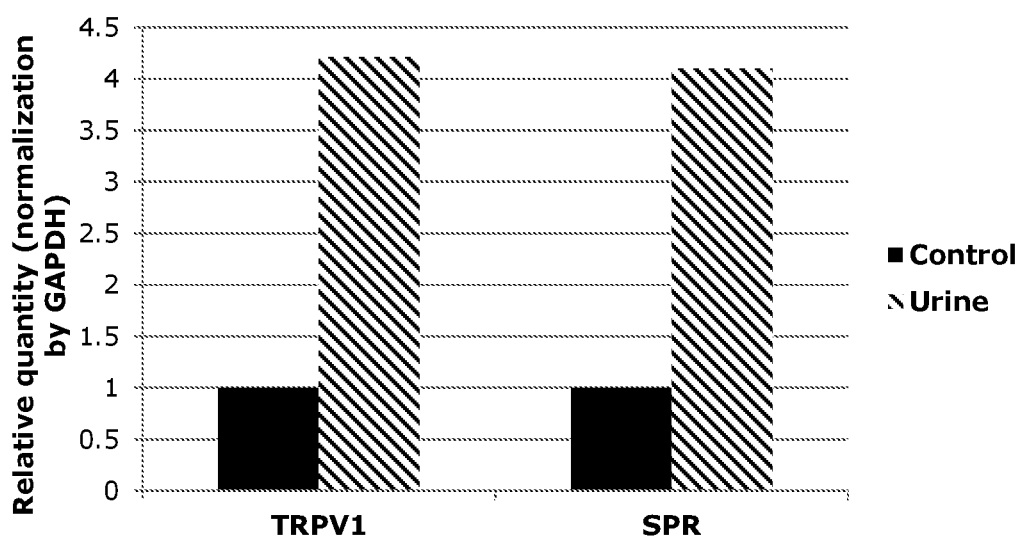

Moreover, urine induced the overexpression of genes, lipid inflammation markers (PTGS2, enzyme of the prostaglandins synthesis pathway), protein inflammation markers (IL1alpha and IL8) and neurogenic inflammation markers (substance P receptor, SPR, and TRPV1) (FIGS. 2, 3 and 4, respectively).

1.3.2. Barrier Function

The outermost layer of the epidermis, the stratum corneum (SC), constitutes, thanks to its particular structure, a protective barrier against environmental attacks. The SC is the final product of epidermal differentiation, where keratinocytes are transformed into corneocytes; these corneocytes being coated with an intercellular lipid matrix composed of ceramides, cholesterol and essential fatty acids. After extrusion of the lamellar bodies, the lipid precursors are metabolized to mature lipids. In the case of the ceramide precursors, it is the enzymes acid sphingomyelinase and beta glucocerebrosidase which transform them into ceramides 2 and 5 (for sphingomyelinase) and into ceramides 1, 3, 4, 6, 7, 8 and 9 (for glucocerebrosidase). Corneocytes are surrounded by a protein cornified envelope composed of numerous proteins such as involucrin, loricrin, small proline-rich proteins and sciellin in particular, solidly joined together by the action of transglutaminases.

Corneodesmosomes are modified, specialized desmosomes which attach cells to each other in the SC and ensure their cohesion. Corneodesmosomes are composed of transmembrane glycoproteins such as desmoglein 1, desmocollin 1 and corneodesmosin.

The epidermal barrier function is principally provided by the stratum corneum, and intercellular lipids and corneodesmosomes and the cornified envelope of corneocytes are its key components.

However, beneath the SC, tight junctions constitute a second line of the barrier function. They form at the level of the stratum granulosum anchor points between cells, forming a physical barrier at the apical pole of the cells. These junctions thus constitute a selective paracellular diffusion barrier preventing the penetration of harmful molecules. The tight junctions are composed of various transmembrane proteins such as, in particular, claudins, occludin and ZO1.

The barrier functions provided by the SC and the tight junctions are closely linked. Indeed, the alteration of one can influence the formation of the other.

In our experimental conditions, urine induced a decrease in the gene expression of key markers of the barrier function such as involucrin (cornified envelope), acid sphingomyelinase (ceramide maturation), corneodesmosin (corneodesmosome) and claudin 1 (tight junction) (FIG. 5).

1.3.3. Stem Cells

The stem cells of tissue in permanent renewal are classically defined as being rare and relatively quiescent cells. They have a unique capacity of self-renewal and of tissue regeneration which enables them to ensure the homeostasis and integrity of the tissue wherein they reside.

Among epidermal stem cells, interfollicular stem cells located in the basal layer constitute the principal epidermal stem cell reservoir. These cells reside in an anatomical and functional microenvironment, the niche, which helps maintain their characteristics, in particular when physiological conditions change. Interfollicular stem cells and their niches are involved in maintaining epidermal integrity and regeneration.

The stem cells are identifiable only by following several markers:

Keratin 19 is a marker of proliferation of stem cells maintaining their characteristics.

Integrins beta 1, beta 4 and alpha 6 (cell surface receptors) are identified as markers of stem cells, and more particularly of the interaction with their niche. They also help regulate the processes of differentiation and proliferation Survivin (BIRC5) is a marker of stem cells regulating the cell cycle. Marker of resistance to apoptosis, it has a role in the survival of stem cells faced with attacks (like UV).

Lrig1 is an epidermal growth factor receptor antagonist and a marker maintaining the quiescent stem cells.

Treatment with artificial urine strongly limited the expression of several markers characteristic of stem cells and of their niche (FIG. 6).

Treatment with an artificial urine preparation of epidermises reconstructed with skin cells of 1-year-old infants made it possible to show, in these experimental conditions, that urine has a harmful effect on barrier function markers and on stem cell markers. Moreover, urine induced significant inflammation involving various pathways, on the one hand nonspecific inflammation with various protein and lipid markers and, on the other, neurogenic inflammation.

Once validated, this model was used to evaluate the efficacy of cosmetic products formulated for application during a diaper change on the buttocks area of infants.

2. Evaluation of the Efficacy of Cosmetic Diaper-Change Products on the Model of Reconstructed 1-Year-Old Infant Epidermises "Attacked" with Artificial Urine 2.1. Material and Methods Epidermises were reconstructed in the same manner as described above.

Reconstructed epidermises derived from keratinocytes of the skin of 1-year-old infants were or were not treated topically with the test products and were incubated for 24 hours. After incubation, the epidermises again were or were not treated topically with the test products and then were exposed to the artificial urine (also applied topically). The RHEs were then incubated overnight (16 hours). All the experimental conditions were carried out with n=4.

Four cosmetic diaper-change products, of distinct formulations, were tested and named P1, P2, P3 and P4.

These products are described in Tables 1 to 4, respectively.

The assay of the inflammatory mediator PGE2 in the culture supernatants and the analysis of the differential expression of genes were carried out as described above.

For each sample, the expression level of the gene of interest is normalized by the expression level of the most stable reference gene, which in these experimental conditions is the GAPDH gene. The calculation of relative quantities was carried out as described above.

After calculation of the relative quantities of the genes of interest in the various conditions, Control (without urine, without test product), Urine (without test product) and Product P (test product+urine), the percentage of modulation (stimulation or inhibition) exerted by the test product on the harmful effect of urine is calculated according to the following formulas:

$$\text{Stimulation (\%)} = (RQ_{test\ product} - RQ_{urine}) \times 100$$

$$\text{Inhibition (\%)} = (RQ_{urine} - RQ_{test\ product}) \times 100$$

Statistical analysis to calculate the significance of the results: between-group comparisons were carried out using the unpaired bilateral Student's t-test; *$p<0.05$;  $p<0.01$; * $p<0.001$.

2.2. Results and Conclusion 2.2.1. Inflammation

TABLE 8

% inhibition of the expression of the IL1A and IL8 genes by the test products (compared to urine)

| Test product | IL1A | IL8 | Mean Inhibition Protein Infl. IL1 and IL8 | Significance |
|---|---|---|---|---|
| P1 | 43 | 29 | 36 | * |
| P2 | 24 | 15 | 20 | |
| P3 | 32 | 30 | 31 | * |
| P4 | 39 | 0 | 20 | |

Only products P1 and P3 inhibit IL1A and IL8.

TABLE 9

% inhibition of the expression of the PTGS2 gene and the production of PGE2 by the test products (compared to urine)

| Test product | PGE2 | PTGS2 | Mean Lipid Infl. PGE2 and PTGS2 | Significance |
|---|---|---|---|---|
| P1 | 75 | 88 | 82 | ** |
| P2 | 103 | 74 | 89 | *** |
| P3 | 28 | 76 | 52 | * |
| P4 | 58 | 75 | 67 | * |

All the products inhibit the lipid markers. P2 and P1 perform best.

TABLE 10

% inhibition of the expression of the TRPV1 and SPR genes by the test products (compared to urine)

| Test product | TRPV1 | SPR | Mean Neurogenic Infl. | Significance |
|---|---|---|---|---|
| P1 | 89 | 51 | 70 | *** |
| P2 | 65 | 23 | 44 | ** |
| P3 | 72 | 0 | 36 | |
| P4 | 93 | 30 | 62 | ** |

All the products, except P3, effectively inhibit the markers of neurogenic inflammation, P1 being most effective.

TABLE 11

% inhibition of inflammation (mean % for all the inflammatory markers)

| Test product | % Inhibition of Inflammation (total) | Significance | RANK |
|---|---|---|---|
| P1 | 63 | ** | 1 |
| P2 | 51 | * | 2 |
| P3 | 40 | | 4 |
| P4 | 49 | * | 3 |

This analysis of the inflammation markers makes it possible to show on the one hand the relative efficacy of the test products to modulate inflammation induced by urine and, on the other, to rank the products according to their efficacy.

P1>P2>P4>P3. Product P1 is the only product able to inhibit all the inflammation markers, of whatever type, to a significant degree.

2.2.2. Barrier

TABLE 12

% stimulation of barrier markers by the test products (compared to urine)

| Test product | IVL | Significance | CDSN | Significance | SMPD1 | Significance | CLDN1 | Significance |
|---|---|---|---|---|---|---|---|---|
| P1 | 123 | ** | 64 | *** | 106 | *** | 41 | ** |
| P2 | 226 | *** | 32 | * | 51 | ** | 23 | * |
| P3 | 74 | * | −14 | | 115 | *** | −21 | |
| P4 | 80 | * | 31 | | 90 | *** | 2 | |

Products P1 and P2 perform well to stimulate the expression of the various barrier markers, and P1 stimulates all the markers to a greater degree, except for the greater stimulation of involucrin by P2. Products P3 and P4 have no effect on the markers corneodesmosin and claudin 1.

TABLE 13

% stimulation of barrier markers (mean % for all the barrier markers)

| Test product | % Barrier Function Protection/Strengthening | Significance | RANK |
|---|---|---|---|
| P1 | 84 | *** | 1 |
| P2 | 83 | ** | 2 |
| P3 | 39 | * | 4 |
| P4 | 51 | * | 3 |

This analysis of the barrier markers makes it possible to show on the one hand the relative efficacy of the test products to strengthen and protect the barrier altered by urine and, on the other, to classify the products according to their efficacy.

P1>P2>P4≥P3. Product P1 is the most effective product for strengthening and protecting the epidermal barrier.

2.2.3. Stem Cells

TABLE 14

% stimulation of stem cell markers by the test products (compared to urine)

| Test product | KRT 19 | ITGB1 | ITGA6 | ITGB4 | BIRC5 | Lrig1 |
|---|---|---|---|---|---|---|
| P1 | 93 *** | 62 ** | 45 * | 90 *** | 48 ** | 91 ** |
| P2 | 51 * | 83 *** | 77 * | 66 ** | 14 | 27 * |
| P3 | 116 *** | 33 | 20 | −6 | 48 ** | 32 * |
| P4 | 80 *** | 78 * | 36 * | −43 | 42 ** | 73 * |

To identify interfollicular stem cells in the epidermis it is important to follow in parallel several markers specific to stem cells and to their niche. The test products stimulate to varying degrees the expression of the markers KRT19, ITGB1, A6 and B4, BIRC5 and Lrig1 altered by urine. P1 stimulates in a significant manner all the stem cell markers. P2 and P4 stimulate five of the six stem cell markers. P3 acts only on three of the markers.

TABLE 15

% stimulation of stem cell markers (mean % for all the stem cell markers)

| Test product | % Stem cell protection | Significance | RANK |
|---|---|---|---|
| P1 | 71 | ** | 1 |
| P2 | 53 | * | 2 |

TABLE 15-continued

% stimulation of stem cell markers (mean % for all the stem cell markers)

| Test product | % Stem cell protection | Significance | RANK |
|---|---|---|---|
| P3 | 40 | * | 4 |
| P4 | 44 | * | 3 |

This analysis of the stem cell markers makes it possible to show on the one hand the relative efficacy of the test products in protecting stem cells altered by urine and, on the other, to classify the products according to their efficacy.

P1>P2>P4≥P3. Product P1 is the most effective product in protecting stem cells of the basal layer of the epidermis.

The invention claimed is:

1. A method, comprising:
a) contacting an active agent or a formulation with a reconstructed skin model, said model being obtained from a skin sample from a child;
b) contacting the reconstructed skin model after step a) with urine; and
c) measuring the expression level of at least one biological marker in the skin model after step b), wherein said biological marker is:
   a skin inflammation marker selected from the group consisting of prostaglandin E2, PTGS2, IL-8, TRPV1 and SPR;
   a barrier function marker selected from the group consisting of CNDSM, IVL, SMPD and CLDN1; or
   a stem cell marker selected from the group consisting of KRT19, BIRC5, LRIG1, ITGA6, ITGB1 and ITGB4;
d) measuring a reference expression level of said at least one biological marker in a control reconstituted skin model,
   wherein said control reconstituted skin model has not been contacted with the candidate active agent or the formulation and has not been contacted with urine, or
   wherein said control reconstituted skin model has not been contacted with the candidate active agent or the formulation and has been contacted with urine, or
   wherein said control reconstituted skin model has been contacted with a reference active agent or formulation and has been contacted with urine, or
   wherein said control reconstituted skin model has been contacted with urine and has neither been contacted with the candidate active agent or the formulation nor been contacted with a reference active agent or formulation;
e) preparing a cosmetic or pharmaceutical composition for preventing and/or reducing the harmful effects of urine and suited to children' skin, comprising the active agent or formulation of step a);

wherein:
(i) the expression level of said at least one biological marker measured in step c) is less than or equal to the reference expression level of said at least one biological marker measured in step d) when said at least one biological marker is a skin inflammation marker, or
(ii) the expression level of said at least one biological marker measured in step c) is greater than or equal to the reference expression level of said at least one biological marker measured in step d) when said at least one biological marker is a barrier function marker or stem cell marker.

2. The method of claim 1, further comprising:
f) measuring the cell viability in the skin model and in the control skin model wherein:
(i) the cell viability in the skin model of step b) is greater than or equal to the cell viability in control skin model of step d); and, and the expression level of said at least one biological marker measured in step c) is less than or equal to the reference expression level of said at least one biological marker measured in step d) when said at least one biological marker is a skin inflammation marker; or
(ii) the cell viability in the skin model of step b) is greater than or equal to the cell viability in control skin model of step d), and the expression level of said at least one biological marker measured in step c) is greater than or equal to the reference expression level of said at least one biological marker measured in step d) when said at least one biological marker is a barrier function marker or a stem cell marker.

3. The method of claim 1, wherein step c) comprises the measurement of a combination of biological markers, said combination comprising:
at least one skin inflammation marker and at least one barrier marker; or
at least one skin inflammation marker and at least one stem cell marker; or
at least one barrier marker and at least one stem cell marker.

4. The method of claim 1, wherein step c) comprises the measurement of a combination of biological markers, said combination comprising at least one skin inflammation marker and at least one barrier marker and at least one stem cell marker.

5. The method of claim 1, wherein the skin sample comes from a donor selected from the group consisting of newborns, between 0 and 1 month of age, infants, between 1 month and 2 years of age, and children, between 2 years and 16 years of age.

6. The method of claim 1, wherein the reconstructed skin model is selected from suspended skin cell cultures, monolayer skin cell cultures, bilayer skin cell cultures, reconstructed skin cultures and reconstructed mucosal cultures.

7. The method of claim 1, wherein the cells of the reconstructed skin model come from a skin tissue explant or from stem cells differentiated into skin cells.

8. The method of claim 1, wherein the reconstructed skin model comprises fibroblasts or keratinocytes.

9. The method of claim 1, further comprising administering an effective amount of the cosmetic or pharmaceutical composition of step e) to a human patient for preventing or reducing the harmful effects of urine on patient's skin.

10. The method of claim 2, further comprising administering an effective amount of the cosmetic or pharmaceutical composition of step e) to a human patient for preventing or reducing the harmful effects of urine on patient's skin.

11. A method, comprising:
a) contacting a reconstructed skin model with urine, said model being obtained from a skin sample from a child;
b) contacting an active agent or a formulation with the reconstructed skin model after step a); and
c) measuring the expression level of at least one biological marker in the skin model after step b), wherein said biological marker is:
a skin inflammation marker selected from the group consisting of prostaglandin E2, PTGS2, IL-8, TRPV1 and SPR;
a barrier function marker selected from the group consisting of CNDSM, IVL, SMPD and CLDN1; or
a stem cell marker selected from the group consisting of KRT19, BIRC5, LRIG1, ITGA6, ITGB1 and ITGB4;
d) measuring a reference expression level of said at least one biological marker in a control reconstituted skin model,
wherein said control reconstituted skin model has not been contacted with the candidate active agent or the formulation and has not been contacted with urine, or
wherein said control reconstituted skin model has not been contacted with the candidate active agent or the formulation and has been contacted with urine, or
wherein said control reconstituted skin model has been contacted with a reference active agent or formulation and has been contacted with urine, or
wherein said control reconstituted skin model has been contacted with urine and has neither been contacted with the candidate active agent or the formulation nor been contacted with a reference active agent or formulation;
e) preparing a cosmetic or pharmaceutical composition for preventing and/or reducing the harmful effects of urine and suited to children' skin, comprising the active agent or formulation of step b);
wherein:
(i) the expression level of said at least one biological marker measured in step c) is less than or equal to the reference expression level of said at least one biological marker measured in step d) when said at least one biological marker is a skin inflammation marker, or
(ii) the expression level of said at least one biological marker measured in step c) is greater than or equal to the reference expression level of said at least one biological marker measured in step d) when said at least one biological marker is a barrier function marker or stem cell marker.

12. The method of claim 11, further comprising:
f) measuring the cell viability in the skin model of step b) and in the control skin model of step d);
wherein:
(i) the cell viability in the skin model of step b) is greater than or equal to the cell viability in control skin model of step d), and the expression level of said at least one biological marker measured in step c) is less than or equal to the reference expression level of said at least one biological marker measured in step d) when said at least one biological marker is a skin inflammation marker; or
(ii) the cell viability in the skin model of step b) is greater than or equal to the cell viability in control skin model of step d), and the expression level of said at least one biological marker measured in step c) is greater than or equal to the reference expression level of said at least one biological marker measured in step d) when said at least one biological marker is a barrier function marker or a stem cell marker.

13. The method of claim 11, wherein step c) comprises the measurement of a combination of biological markers, said combination comprising:
   at least one skin inflammation marker and at least one barrier marker; or
   at least one skin inflammation marker and at least one stem cell marker; or
   at least one barrier marker and at least one stem cell marker.

14. The method of claim 11, wherein step c) comprises the measurement of a combination of biological markers, said combination comprising at least one skin inflammation marker and at least one barrier marker and at least one stem cell marker.

15. The method of claim 11, wherein the skin sample comes from a donor selected from the group consisting of newborns, between 0 and 1 month of age, infants, between 1 month and 2 years of age, and children, between 2 years and 16 years of age.

16. The method of claim 11, wherein the reconstructed skin model is selected from suspended skin cell cultures, monolayer skin cell cultures, bilayer skin cell cultures, reconstructed skin cultures and reconstructed mucosal cultures.

17. The method of claim 11, wherein the cells of the reconstructed skin model come from a skin tissue explant or from stem cells differentiated into skin cells.

18. The method of claim 11, wherein the reconstructed skin model comprises fibroblasts or keratinocytes.

19. The method of claim 11, further comprising administering an effective amount of the cosmetic or pharmaceutical composition of step e) to a human patient for preventing or reducing the harmful effects of urine on patient's skin.

20. The method of claim 12, further comprising administering an effective amount of the cosmetic or pharmaceutical composition of step e) to a human patient for preventing or reducing the harmful effects of urine on patient's skin.

21. A method, comprising:
   a) contacting an active agent or a formulation with a reconstructed skin model, said model being obtained from a skin sample from a child, wherein the skin sample comes from a donor selected from the group consisting of newborns, between 0 and 1 month of age, infants, between 1 month and 2 years of age, and children, between 2 years and 16 years of age;
   b) contacting the reconstructed skin model after step a) with urine; and
   c) measuring the expression level of at least one biological marker in the skin model after step b), wherein said biological marker is:
      a skin inflammation marker selected from the group consisting of prostaglandin E2, PTGS2, TRPV1 and SPR;
      a barrier function marker selected from the group consisting of CNDSM, IVL, SMPD and CLDN1; or
      a stem cell marker selected from the group consisting of KRT19, BIRC5, LRIG1, ITGA6, ITGB1 and ITGB4;
   d) measuring a reference expression level of said at least one biological marker in a control reconstituted skin model,
      wherein said control reconstituted skin model has not been contacted with the candidate active agent or the formulation and has not been contacted with urine, or
      wherein said control reconstituted skin model has not been contacted with the candidate active agent or the formulation and has been contacted with urine, or
      wherein said control reconstituted skin model has been contacted with a reference active agent or formulation and has been contacted with urine, or
      wherein said control reconstituted skin model has been contacted with urine and has neither been contacted with the candidate active agent or the formulation nor been contacted with a reference active agent or formulation;
   e) preparing a cosmetic or pharmaceutical composition for preventing and/or reducing the harmful effects of urine and suited to children' skin, comprising the active agent or formulation of step a);
   wherein:
      (i) the expression level of said at least one biological marker measured in step c) is less than or equal to the reference expression level of said at least one biological marker measured in step d) when said at least one biological marker is a skin inflammation marker, or
      (ii) the expression level of said at least one biological marker measured in step c) is greater than or equal to the reference expression level of said at least one biological marker measured in step d) when said at least one biological marker is a barrier function marker or stem cell marker.

\* \* \* \* \*